US012737880B2

(12) United States Patent
Jaber et al.

(10) Patent No.: US 12,737,880 B2
(45) Date of Patent: Sep. 15, 2026

(54) SYSTEMS AND METHODS OF ANALYZING MICROBIOMES USING ARTIFICIAL INTELLIGENCE

(71) Applicant: NantCell, Inc., Culver City, CA (US)

(72) Inventors: Mustafa I. Jaber, Culver City, CA (US); Sandip Reddy, Culver City, CA (US); Kamil Wnuk, Culver City (CA)

(73) Assignee: NantCell, Inc., Culver City, CA (US)

( * ) Notice: Subject to any disclaimer, the term of this patent is extended or adjusted under 35 U.S.C. 154(b) by 518 days.

(21) Appl. No.: 18/196,227

(22) Filed: May 11, 2023

(65) Prior Publication Data

US 2023/0368377 A1 Nov. 16, 2023

Related U.S. Application Data

(60) Provisional application No. 63/395,163, filed on Aug. 4, 2022, provisional application No. 63/341,559, filed on May 13, 2022.

(51) Int. Cl.
*G06K 9/00* (2022.01)
*G06T 7/00* (2017.01)
*G16H 50/20* (2018.01)

(52) U.S. Cl.
CPC ........... *G06T 7/0012* (2013.01); *G16H 50/20* (2018.01); *G06T 2207/20081* (2013.01); *G06T 2207/20084* (2013.01); *G06T 2207/30024* (2013.01)

(58) Field of Classification Search
None
See application file for complete search history.

(56) References Cited

U.S. PATENT DOCUMENTS

2019/0050534 A1 2/2019 Apte et al.
2020/0263261 A1 8/2020 Guan et al.
2021/0090694 A1* 3/2021 Colley .................. G16B 30/00
2022/0102000 A1* 3/2022 Segal ..................... G16H 20/60
2023/0062811 A1* 3/2023 Kunz ..................... G16H 30/40
2023/0332249 A1* 10/2023 Poore ..................... G16B 20/00

FOREIGN PATENT DOCUMENTS

JP 2022521191 4/2022
WO WO 2021/141742 7/2021
WO WO 2021/142449 7/2021

OTHER PUBLICATIONS

Poore et al., "Microbiome analyses of blood and tissue suggest cancer diagnostic approach," Nature, Author Manuscript, Mar. 2020, vol. 579(7800), pp. 567-574, 46 pages.
International Search Report and Written Opinion for International (PCT) Patent Application No. PCT/US2023/021874, dated Aug. 4, 2023 15 pages.

(Continued)

*Primary Examiner* — Wei Wen Yang
(74) *Attorney, Agent, or Firm* — Sheridan Ross P.C.

(57) ABSTRACT

Disclosed systems and methods include executing a convolutional neural network to detect a level of microbiome in a whole slide image associated with a patient, based on an output of the convolutional neural network, categorize the whole slide image as one of microbiome-low and microbiome-high, and, based on the categorization of the whole slide image, determine a characteristic of a cancer associated with the patient.

20 Claims, 14 Drawing Sheets

(56) References Cited

OTHER PUBLICATIONS

Cullin et all, "Microbiome and cancer," Cancer Cell, Sep. 9, 2021, vol. 39(10), pp. 1317-1341.

Furusawa et al., "Decoding gut microbiota by imaging analysis of fecal samples," iScience, CellPress, Dec. 17, 2021, pp. 1-14, retrieved from pubmed.ncbi.nlm.hih.gov/34927025, retrieved on Apr. 21, 2025, Dec. 17, 2021, pp. 1-14.

Zeller et al., "Potential of fecal microbiota for early-stage detection of colorectal cancer," Molecular Systems Biology, Nov. 28, 2014, vol. 10(11), pp. 1-18.

Official Action for Japanese Patent Application No. 2024-566310, dated Oct. 28, 2025 9 pages.

* cited by examiner

Test Patients True label

Estimated Probability of Survival 1.0
0.8
0.6
0.4
0.2
0

0 20 40 60 80 100 120

Time (Months)

409

412

SYSTEMS AND METHODS OF ANALYZING MICROBIOMES USING ARTIFICIAL INTELLIGENCE

CROSS-REFERENCE TO RELATED APPLICATIONS

This application claims the benefit of priority under 35 U.S.C. § 119(e) to U.S. Provisional Patent Application No. 63/341,559, filed May 13, 2022, and to U.S. Provisional Patent Application No. 63/395,163 filed Aug. 4, 2022. The entire disclosures of each of U.S. Provisional Patent Application No. 63/341,559 and of U.S. Provisional Patent Application No. 63/395,163 are incorporated herein by reference.

FIELD OF THE DISCLOSURE

The invention relates generally to systems and methods for analyzing image data and particularly to identifying microbiomes in whole slide images and determining relative microbiome levels in hematoxylin and eosin (H&E)-stained images.

BACKGROUND

The human microbiome profoundly influences cancer and plays a role in the progression of carcinogenesis. The microbiome is the community of microorganisms (such as fungi, bacteria, and viruses) that exists in a particular environment. In humans, the term is often used to describe the microorganisms that live in or on a particular part of the body, such as the skin or gastrointestinal tract, or within a specific area, such as the tumor microenvironment (TME). These microorganisms are dynamic and change in number and identity in response to a host of environmental factors, such as exercise, diet, medication, and other exposures.

Recent studies have shown that there are significant microbial contributions in select cancer types, including for example on cancer development, progression, and response to treatment, but the full extent and diagnostic implications of microbial contributions across diverse cancer types remain unknown.

The manual examination of tissue and blood samples, e.g., through the use of a microscope, is fraught with problems such as imprecision, inaccuracy, and inefficiency. Manual examination of tissue and blood samples are inadequate from a patient's point of view as patients are required to make appointments with experts and travel to particular hospitals or clinics to provide samples.

The human microbiome profoundly influences cancer and plays a role in the progression of carcinogenesis. These groups of microorganisms are dynamic and change in response to a host of environmental factors, such as exercise, diet, medication, and other exposures.

Recent studies have shown that there are significant microbial contributions in select cancer types but that the extent and diagnostic implications of microbial contributions across diverse cancer types remain unknown.

SUMMARY

There is a need for a system and method capable of automatically and/or remotely diagnosing and/or measuring the severity or stage of cancer within a patient. The human microbiome exerts a profound influence on cancer development, progression, and response to treatment. As described herein, an image-based computational pathology system can be trained to assess the microbiome levels in whole-slide images (WSIs). Such a system may be trained to categorize input WSIs as microbiome-low or microbiome-high. Such categorization may be used to determine a severity of cancer in a patient from which the input WSI was captured. To facilitate microbiome analysis in cancer, as described herein, this disclosure provides an artificial intelligence (AI)-driven computational pathology system configured to determine relative microbiome levels in tissue specimens, including hematoxylin and eosin stain (H&E)-stained slides from formalin-fixed paraffin-embedded tissue samples or biopsies.

Whole-genome and whole-transcriptome sequencing data, which may be utilized for microbiome detection as described herein, may be available in The Cancer Genome Atlas (TCGA) bladder cancer, for which images are available, to define microbiome-low and -high labels.

Systems and methods described herein may be used to determine correlations between microbiome levels as determined by an AI system and treatment responses in patients such as non-muscle invasive bladder cancer patients. Such correlations may be used to determine, based on microbiome levels as determined by an AI system, a severity of cancer in a patient. By comparing WSIs captured for a patient at different times, a level of progression of cancer may be assessed.

As described herein, a TCGA bladder cancer cohort may be distributed into training, validation, and test sets; each with equal numbers of microbiome-low and -high patients. The cohort may feature an average of one or more diagnostic (DX) images per patient, with hundreds of DX images in total. In an exemplary study provided in this disclosure, the TCGA bladder cancer cohort (n=408) was distributed into training (66.7%, n=272), validation (8.3%, n=34), and test (25.0%, n=102) sets; each with equal numbers of microbiome-low and -high patients. The cohort featured an average of 1.05 DX images per patient, with 429 DX images in total.

In accordance with one or more of the embodiments described herein, a deep network may be trained using hundreds or thousands of patches randomly selected from hundreds of diagnostic images in a training set. Testing on untouched (i.e., raw, unredacted, unedited) patient data provides for an area under the Receiver Operator Characteristic (ROC) curve greater than about 0.7 and an F1 score of greater than about 0.7. This disclosure provides an exemplary study in which a deep network was trained using a total of 303,104 patches (of size 100×100 microns, equivalent to 400×400 pixels at 40× magnification) randomly selected from 296 DX images in the training set. Testing on untouched patient data (n=102) provided an area under the ROC curve of 0.74 and an F1 score of 0.74.

In general, aggregating results from three different training checkpoints per CNN may result in greater stability for performance on validation sets. Table 1 below shows evaluation metrics on three top checkpoints per CNN using the validation set. An ensemble of the top three checkpoints is also included per CNN.

TABLE 1

Microbiome-detection application performance for TCGA bladder cancer validation set (34 WSIs).

| CNN | Checkpoint | ROC-AUC | PR-AUC | Optimal threshold | Precision | Recall | F1 score |
|---|---|---|---|---|---|---|---|
| Inception v3 | Epoch 3, Step 0 | 0.72 | 0.71 | 0.22 | 0.75 | 0.71 | 0.73 |
| | Epoch 4, Step 5000 | 0.75 | 0.72 | 0.38 | 0.72 | 0.76 | 0.74 |
| | Epoch 5 Step 5000 | 0.76 | 0.68 | 0.4 | 0.75 | 0.71 | 0.73 |
| | Ensemble result | 0.77 | 0.74 | 0.43 | 0.85 | 0.65 | 0.73 |
| ResNet-152 | Epoch 6, Step 0 | 0.77 | 0.69 | 0.1 | 0.7 | 0.94 | 0.8 |
| | Epoch 7, Step 0 | 0.75 | 0.71 | 0.39 | 0.72 | 0.76 | 0.74 |
| | Epoch 10, Step 0 | 0.73 | 0.7 | 0.21 | 0.68 | 0.88 | 0.77 |
| | Ensemble result | 0.75 | 0.7 | 0.27 | 0.71 | 0.71 | 0.71 |
| DenseNet-201 | Epoch 2, Step 0 | 0.76 | 0.75 | 0.68 | 0.92 | 0.65 | 0.76 |
| | Epoch 6, Step 5000 | 0.77 | 0.68 | 0.75 | 0.82 | 0.82 | 0.82 |
| | Epoch 8 Step 5000 | 0.73 | 0.67 | 0.48 | 0.75 | 0.71 | 0.73 |
| | Ensemble result | 0.82 | 0.78 | 0.71 | 0.93 | 0.76 | 0.84 |

Areas under the ROC curve and under the Precision-Recall curve using Inception v3, ResNet-152, and DenseNet-201 ensemble systems range from 0.77 to 0.82 (ROC-AUC), and from 0.70 to 0.78 (PR-AUC), with DenseNet-201 achieving the best results on the TCGA validation set.

In the methods and systems of this disclosure, a developed AI system may be used to determine correlations between TCGA bladder cancer patient survival and microbiome level. For example, treatment-naïve bladder cancer patients identified as microbiome-low by an image-based system of this disclosure were seen to have higher survival rates, with hazard ratio of 1.45.

Further, correlations between pathologic complete response (pCR) may be assessed days, weeks, months, or even years after diagnosis or treatment, and a microbiome level in non-muscle invasive bladder cancer patients in clinical trials is obtained. Patients that achieved a pCR with treatment may be found to have significantly higher probability of microbiome-high pre-treatment, as compared to those who did not achieve a pCR. Reductions in predicted microbiome levels after treatment may be observed in pCR patients. Conversely, non-responders may be found to have an increase in microbiome-high probability with treatment.

As described herein, a novel AI-driven image-based computational pathology system has the potential to provide data that may not only inform clinical decision-making, but also allow further investigation into the role of the TME microbiome in cancer. An AI-driven image-based microbiome analysis system and methods of this disclosure may be used to reveal correlations of higher pre-treatment microbiome level with complete response in trial patients.

These and other needs are addressed by the various embodiments and configurations of this disclosure. These systems and methods of this disclosure provide a number of advantages depending on the particular configuration, and these and other advantages will be apparent from this disclosure.

As described herein, systems and methods may be used to analyze microbiomes in images of blood and/or tissue samples and, based on the analysis, perform cancer pathology, such as cancer diagnosis and staging, i.e., describing the extent of cancer within a patient from whom the images are captured, and to determine treatment options for the patient. Such systems and methods may be used, for example, for diagnosing the stage or severity of bladder cancer within a patient.

As described herein, an image-based system utilizing a convolutional neural network (CNN) may be configured to detect microbiome in H&E-stained pathology slides of frozen tissue.

One or more means for performing any one or more of the above embodiments or aspects of the embodiments are described herein.

This disclosure includes any aspect in combination with any one or more other aspects.

This disclosure includes any one or more of the features disclosed herein.

This disclosure includes any one or more of the features as substantially disclosed herein.

This disclosure includes any one or more of the features as substantially disclosed herein in combination with any one or more other features as substantially disclosed herein.

This disclosure includes any one of the aspects/features/embodiments in combination with any one or more other aspects/features/embodiments.

This disclosure provides the use of any one or more of the aspects or features as disclosed herein.

It is to be appreciated that any feature described herein can be claimed in combination with any other feature(s) as described herein, regardless of whether the features come from the same described embodiment.

The preceding is a simplified summary of the invention to provide an understanding of some aspects of the invention. This summary is neither an extensive nor exhaustive overview of the invention and its various embodiments. It is intended neither to identify key or critical elements of the invention nor to delineate the scope of the invention but to present selected concepts of the invention in a simplified form as an introduction to the more detailed description presented below. As will be appreciated, other embodiments of the invention are possible utilizing, alone or in combination, one or more of the features set forth above or described in detail below. Also, while the disclosure is presented in terms of exemplary embodiments, it should be appreciated that an individual aspect of the disclosure can be separately claimed.

BRIEF DESCRIPTION OF THE DRAWINGS

The present disclosure is described in conjunction with the appended figures, wherein.

DETAILED DESCRIPTION

Figure 1:
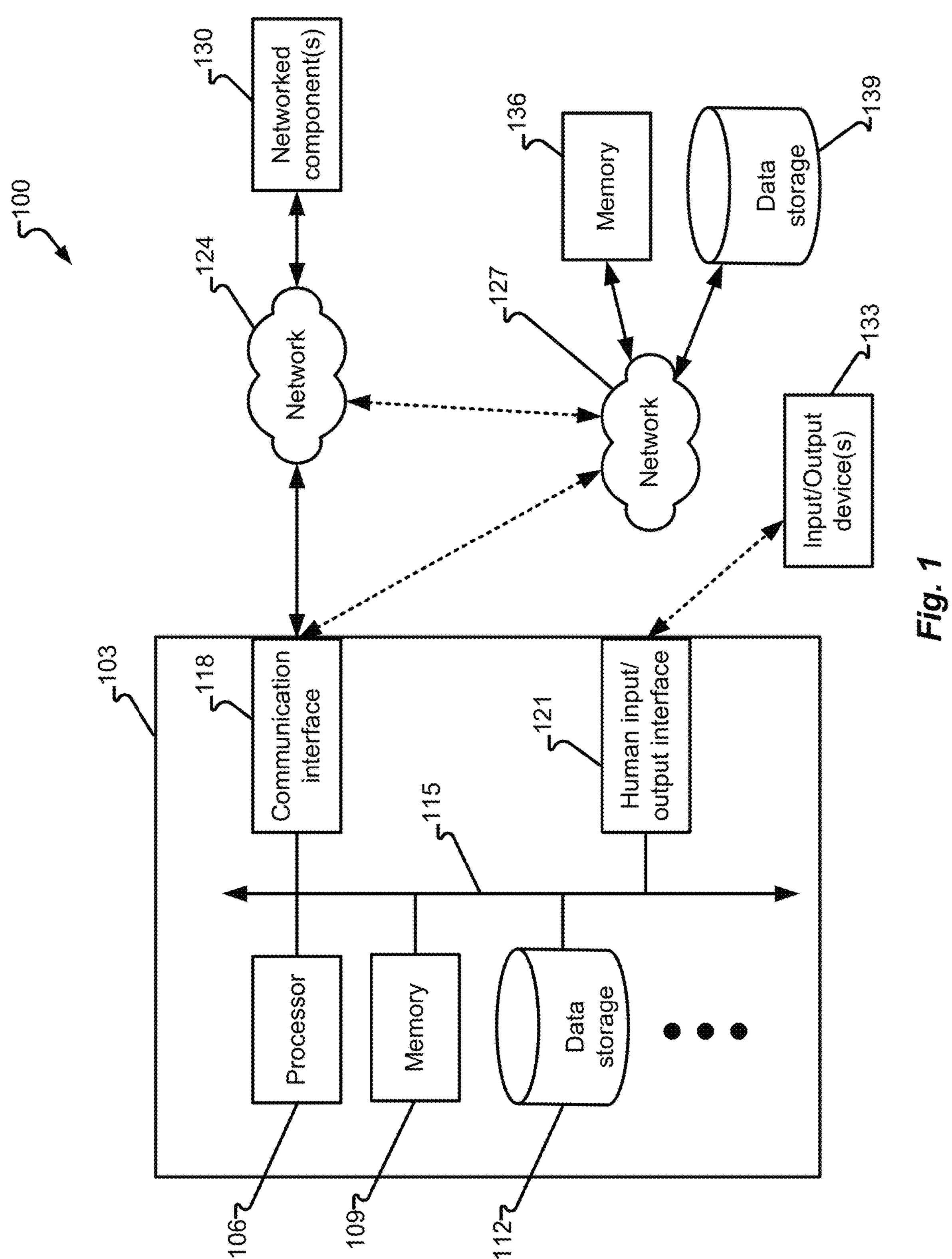
FIG. 1 is an illustration of a computing environment in accordance with one or more of the embodiments described herein.

Systemic human microbiome as well as tumor-microenvironment (TME)-associated human microbiome influence the development and progression of cancer as well as response to therapy, due at least in part to effects on the immune system. As described herein, a system may be configured to determine relative microbiome levels from WSIs such as H&E-stained pathology slides. Based on the relative microbiome levels in images from a patient, the TME microbiome can be analyzed and used to generate an estimated level of cancer in the patient.

Such a system, as described herein, may comprise one or more neural networks such as convolutional neural networks (CNNs). The neural networks may be trained using tumor images which are labeled as microbiome-high or microbiome-low. Such tumor images may be, for example, tumor images from TCGA bladder cancer samples for which whole transcriptome-based microbiome analyses have been performed.

By performing an analysis of biopsy images, such as images from the QUILT 3032 trial (Chamie K, Lee J H, Rock A, et al: Preliminary phase 2 clinical results of IL-15RαFc superagonist N-803 with BCG in BCG-unresponsive non-muscle invasive bladder cancer (NMIBC) patients. J Clin Oncol 37:4561-4561, 2019) of bacillus Calmette-Guerin (BCG) and the interleukin-15 superagonist N-803 (nogapendekin alfa inbakicept; NAI) in BCG-unresponsive non-muscle invasive bladder cancer patients, it can be seen that the probability of being microbiome-high at baseline was greater for patients having achieved a complete response (CR) with therapy than in those without having achieved a CR.

These findings, along with the increased efficiency of the image-based analysis system described herein, empower an application to provide insight into relationships between microbiome level and response to therapy in cancer patients. Using a system as described herein, the microbiome level in tumor tissue pathology images may be assessed and an association between microbiome level and response to therapy may be used as a useful tool for studying such relationships and to inform therapeutic decision-making.

Using a system as described herein, a microbiome level may be estimated using one or more neural networks based on input images in bladder cancer. Although morphological alterations that the microbiome introduces to solid tumor tissue may be too fine to readily discriminate by eye, even by a trained pathologist, a system as described herein is capable of identifying visual patterns that distinguish tissues with high microbiome load.

The microbiome, comprising a range of microbiota (bacteria, fungi, etc.), in combination with the theatre of activity, including proteins, peptides, nucleic acids, polysaccharides, toxins, and signaling molecules, associated with the microbiota of the human gut and specifically of tumor microenvironment (TME) exerts a profound influence on the development of cancer and response to therapy. This relationship may be based on microbiome effects on tumor initiation and progression as well as the immune system.

A conventional method for assessment of some components of the TME microbiome is by immunohistochemical analysis, but this method is inherently limited by the number of microbiota-directed antibodies that can be used. As an alternative, microbiome analysis based on whole genome and transcriptome sequencing has become more widely utilized but is not applied as part of standard diagnosis. A recent study, Poore, G. D., Kopylova, E., Zhu, Q. et al., Nature 579, 567-574 (2020), ("Poore et al."), which is incorporated by reference herein, e-examined whole-genome and whole-transcriptome sequencing data from treatment-naïve patients across thirty-three cancer types in the Cancer Genome Atlas (TCGA) for microbial reads, and identified the majority of samples showing evidence of specific microbial signatures uniquely corresponding to cancer. Poore et al. found that most samples from a certain type of cancer show significant intensities in a few microbiomes.

As disclosed herein, to facilitate the feasibility and thus utility of TME microbiome analysis as a biomarker, the analysis of Poore et al. in our development of a computational approach to detection of microbiome levels in hematoxylin and eosin (H&E) stained tissue section images. First TCGA bladder cancer images based on data from Poore et al. were classified as microbiome-low or microbiome-high. Next, a CNN-based system as described herein was trained based on the classified samples. Next, the performance of the CNN-based system was evaluated based on its outputs when provided independent patient samples as inputs. Finally, the CNN-based system was then used to assess associations between baseline, pre-treatment TME microbiome-level and response to therapy in patients in a clinical trial of a novel interferon-15 superagonist N-803 (nogapendekin alfa inbakicept, NAI) in combination with *bacillus* Calmette-Guerin (BCG) in BCG-unresponsive non-muscle-invasive bladder cancer.

Using a system or method as described herein, microbiome information may be identified from input whole slide images (WSIs) using systems and methods described herein. The systems and methods described herein use a trained neural network such as a CNN to identify microbiome characteristics and locate microbiome pixels from within one or more patches generated from an input WSI. In certain embodiments, a certainty as to whether the WSI or patch contains a particular amount of microbiome may be generated. The microbiome characteristics identified by the CNN may be used to determine a stage or severity of a cancer. While bladder, and other cancer types are described herein as examples, it should be appreciated the systems and methods described herein may be adapted to any type of cancer and/or particular types of microbiomes.

The systems and methods described herein apply a deep learning-based system to assess tumor tissue images to characterize microbiome probability and response in patients. Such analysis may be extended to any type of cancer and/or may be used to implement a pan-cancer microbiome level detector. Further, a system as described herein may be used not only to detect high or low microbiome levels but also to differentiate between microbial types such as to generate a series of microbial and theater of action signatures. Such a system may be used to assess not only the response to therapy in a variety of tumor types and therapeutic approaches, but also prognosis and likelihood of metastasis, and reveal characteristics of the TME microbiome optimal for response to therapy. Such an application has the potential to become a feasible method by which to help guide physician decision-making for cancer patients. As described herein, systems and methods of determining one or more characteristics of a cancer associated with a patient may be determined. Such characteristics may include, for example, factors such as the stage of cancer, grade of cancer and/or tumor, location of cancer and/or tumor, presence of metastases, expression of biomarkers likely to lead to therapeutic or immune evasion (such as heightened presence of PD-L1 expression in the tumor), and distribution of lymphocytes and other immune cell types within the tumor environment. Different types of cancer, such as bladder cancer, head and neck cancer, and ovarian cancer, may be associated with different characteristics that can be used to determine their severity. As used herein, characteristic may refer to any one or more of any such factors.

The ensuing description provides embodiments only and is not intended to limit the scope, applicability, or configuration of the claims. Rather, the ensuing description will provide those skilled in the art with an enabling description for implementing the embodiments. It will be understood that various changes may be made in the function and arrangement of elements without departing from the spirit and scope of the appended claims.

Any reference in the description comprising a numeric reference number, without an alphabetic sub-reference identifier when a sub-reference identifier exists in the figures, when used in the plural, is a reference to any two or more elements with the like reference number. When such a reference is made in the singular form, but without identification of the sub-reference identifier, is a reference to one of the like numbered elements, but without limitation as to the particular one of the elements being referenced. Any explicit usage herein to the contrary or providing further qualification or identification shall take precedence.

The exemplary systems and methods of this disclosure will also be described in relation to analysis software, modules, and associated analysis hardware. However, to avoid unnecessarily obscuring the present disclosure, the following description omits well-known structures, components, and devices, which may be omitted from or shown in a simplified form in the figures or otherwise summarized.

The phrases "at least one," "one or more," "or," and "and/or" are open-ended expressions that are both conjunctive and disjunctive in operation. For example, each of the expressions "at least one of A, B, and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B, and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Aspects of the present disclosure may take the form of an embodiment that is entirely hardware, an embodiment that is entirely software (including firmware, resident software, micro-code, etc.) or an embodiment combining software and hardware aspects that may all generally be referred to herein as a "circuit," "module," or "system." Any combination of one or more computer-readable medium(s) may be utilized. The computer-readable medium may be a computer-readable signal medium or a computer-readable storage medium.

A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible, non-transitory medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device. Program code embodied on a computer-readable medium may be transmitted using any appropriate medium, including, but not limited to, wireless, wireline, optical fiber cable, RF, etc., or any suitable combination of the foregoing.

The terms "determine," "calculate," "compute," and variations thereof, as used herein, are used interchangeably, and include any type of methodology, process, mathematical operation, or technique.

The term "means" as used herein shall be given its broadest possible interpretation in accordance with 35 U.S.C., Section 112(f) and/or Section 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary, brief description of the drawings, detailed description, abstract, and claims themselves.

For purposes of explanation, numerous details are set forth in order to provide a thorough understanding of the present disclosure. It should be appreciated, however, that the present disclosure may be practiced in a variety of ways beyond the specific details set forth herein.

FIG. 1 depicts a computer system 103 in a computing environment 100 in accordance with embodiments of the present disclosure. In some embodiments, a method of analyzing whole slide images as described herein may be performed by a computer system 103 existing in a computing environment 100 as illustrated in FIG. 1. In one embodiment, a device for identifying microbiome information in input image data may be embodied, in whole or in part, as computer system 103 comprising various components and connections to other components and/or systems.

The components are variously embodied and may comprise processor 106. The term “processor,” as used herein, refers exclusively to electronic hardware components comprising electrical circuitry with connections (e.g., pinouts) to convey encoded electrical signals to and from the electrical circuitry. Processor 106 may comprise programmable logic functionality, such as determined, at least in part, from accessing machine-readable instructions maintained in a non-transitory data storage, which may be embodied as circuitry, on-chip read-only memory, memory 109, data storage 112, etc., that cause the processor 106 to perform steps of the instructions.

Processor 106 may be further embodied as a single electronic microprocessor or multiprocessor device (e.g., multicore) having electrical circuitry therein which may further comprise a control unit(s), input/output unit(s), arithmetic logic unit(s), register(s), primary memory, and/or other components that access information (e.g., data, instructions, etc.), such as received via bus 115, executes instructions, and outputs data, again such as via bus 115. In other embodiments, processor 106 may comprise a shared processing device that may be utilized by other processes and/or process owners, such as in a processing array within a system (e.g., blade, multi-processor board, etc.) or distributed processing system (e.g., “cloud,” farm, etc.). It should be appreciated that processor 106 is a non-transitory computing device (e.g., an electronic machine comprising circuitry and connections to communicate with other components and devices).

Processor 106 may operate a virtual processor, such as to process machine instructions not native to the processor (e.g., translate an operating system and machine instruction code set to enable applications to execute on a virtual processor), however, as those of ordinary skill understand, such virtual processors are applications executed by hardware, more specifically, the underlying electrical circuitry and other hardware of the processor (e.g., processor 106). Processor 106 may be executed by virtual processors. Virtual processors enable an application to be presented with what appears to be a static and/or dedicated processor executing the instructions of the application, while underlying non-virtual processor(s) are executing the instructions and may be dynamic and/or split among a number of processors.

In addition to the components of processor 106, computer system 103 may utilize memory 109 and/or data storage 112 for the storage of accessible data, such as instructions, values, etc. Communication interface 118 facilitates communication with components, such as processor 106 via bus 115 with components not accessible via bus 115. Communication interface 118 may be embodied as a network port, card, cable, or other configured hardware device. Additionally, or alternatively, human input/output interface 121 connects to one or more interface components to receive and/or present information (e.g., instructions, data, values, etc.) to and/or from a human and/or electronic device. Examples of input/output devices 133 that may be connected to input/output interface include, but are not limited to, keyboard, mouse, trackball, printers, displays, sensor, switch, relay, speaker, microphone, still and/or video camera, etc. In another embodiment, communication interface 118 may comprise, or be comprised by, human input/output interface 121. Communication interface 118 may be configured to communicate directly with a networked component or utilize one or more networks, such as network 124 and/or network 127.

Network 124 may be a wired network (e.g., Ethernet), a wireless network (e.g., Wi-Fi, Bluetooth, cellular, etc.), or a combination thereof and may enable computer system 103 to communicate with networked component(s) 130. In other embodiments, network 124 may be embodied, in whole or in part, as a telephony network (e.g., public switched telephone network (PSTN), private branch exchange (PBX), cellular telephony network, etc.).

Additionally, or alternatively, one or more other networks may be utilized. For example, network 127 may represent a second network, which may facilitate communication with components utilized by computer system 103. For example, network 127 may be an internal network to a business entity or other organization, whereby components are trusted (or at least trusted to a degree), where networked component(s) 130 connected to a public network (e.g., Internet) such as network 124 may not be trusted (or at least trusted to a lesser degree).

Components attached to network 127 may include memory 136, data storage 139, input/output device(s) 133, and/or other components that may be accessible to processor 106. For example, memory 136 and/or data storage 139 may supplement or supplant memory 109 and/or data storage 112 entirely or for a particular task or purpose. As another example, memory 136 and/or data storage 139 may be an external data repository (e.g., server farm, array, “cloud,” etc.) and enable computing device 103, and/or other devices, to access data thereon. Similarly, input/output device(s) 133 may be accessed by processor 106 via human input/output interface 121 and/or via communication interface 118 either directly, via network 127, via network 124 alone (not shown), or via networks 127 and 124. Each of memory 109, data storage 112, memory 136, data storage 139 comprise a non-transitory data storage comprising a data storage device.

It should be appreciated that computer-readable data may be sent, received, stored, processed, and presented by a variety of components. It should also be appreciated that components illustrated may control other components, whether illustrated herein or otherwise. For example, one input/output device 133 may be a router, switch, port, or other communication component such that a particular output of processor 106 enables (or disables) input/output device 133, which may be associated with network 124 and/or network 127, to allow or disallow communications between two or more nodes on network 124 and/or network 127. One of ordinary skill in the art will appreciate that other communication equipment may be utilized, in addition or as an alternative, to those described herein without departing from the scope of the embodiments.

As a result, and in one embodiment, processor 106 may execute instructions to perform the systems and methods described herein. In another embodiment, networked component(s) 130 may execute one or more systems and methods while processor 106 may execute one or more other systems and methods. Memory values may be read from memory 109 or a memory of one or more network component(s) 130. In another embodiment, outputs from systems and methods as described herein may be maintained in memory 136 and/or data storage 139.

Figure 2:
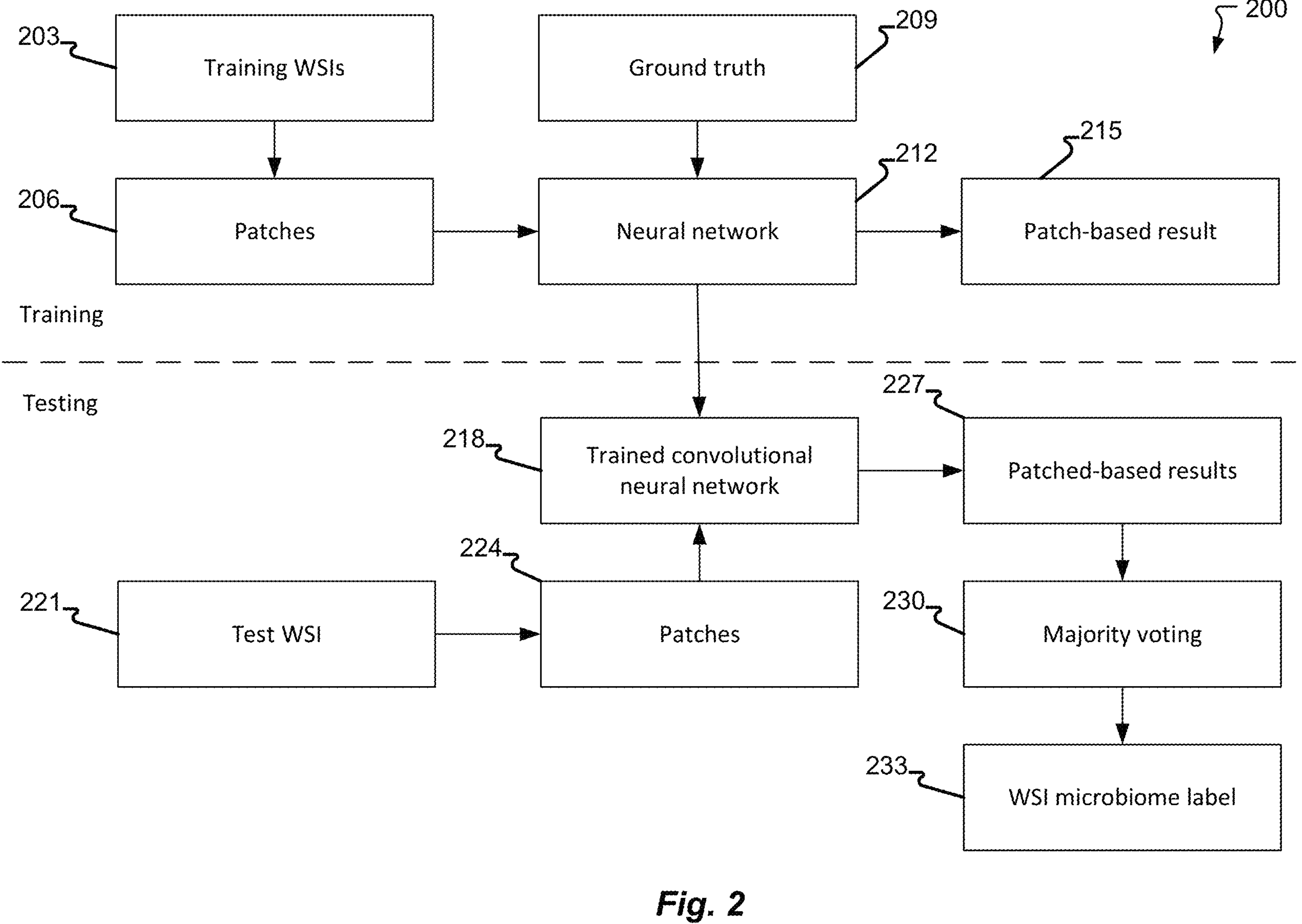
FIG. 2 is a block diagram of a machine learning system in accordance with one or more of the embodiments described herein.

The computer system 103 may be configured to execute a machine learning (ML) system 200 as illustrated in FIG. 2. In some embodiments, the ML system 200 may comprise a training element and a testing element. While in other embodiments, the ML system 200 may comprise a pre-trained CNN and may not include a training element.

A training element of the ML system 200 may be used to train a neural network 212 of the ML system 200 to generate patch-based results 215 based on an input of patches 206. The training element of the ML system 200 may be one or more processes executed by a processor 106 based on instructions in memory 109 as illustrated in FIG. 1. The patches 206 may be stored in data storage 112 or received by the computer system 103 via the communication interface 118 and/or may be created from one or more images or WSIs stored in data storage 112 or received by the computer system 103 via the communication interface 118.

A WSI may be associated with a patient. In some embodiments, the method may comprise associating the WSI with a patient in a database. For example, the method may comprise identifying a patient associated with the WSI and determining a level of cancer for the patient at a particular time, such as a time prior to the date of collection of the sample imaged in the WSI.

A WSI may be an image comprising H&E-stained pathology slides. A WSI may be an image of a frozen tissue or blood sample.

Such WSIs may be, for example, formalin-fixed, paraffin-embedded (FFPE) tissue section slide diagnostic images, such as may be available from the Comprehensive Molecular Characterization of Muscle-Invasive Bladder Cancer (BLCA) cancer cohort in TCGA.

Tissue imaged in the images may be stored in an ultra-cold freezer at less than low eighty degrees. By using frozen tissue images, the native non-denatured proteins can be isolated in a still active form for biochemical analysis. In some embodiments, an input to the one or more neural networks comprises a plurality of patches extracted from the WSI. The image may comprise, for example, a 400×400 pixel image with 40× magnification. Each patch of the plurality of patches is 100×100 microns in size. Each patch of the plurality of patches may comprise a one-hundred micrometer square patch. Each patch may be representative of a 100-micrometer square portion of tissue.

Each of the input patches 206 may be related to a patient and/or to a WSI associated with a patient. Generating patch-based results 215 may comprise first pre-processing an input whole slide image (WSI) to break the WSI into a plurality of patches. For example, and as described in greater detail herein, a WSI associated with a patient may be divided into a number of patches. Each of the patches created from a WSI may be associated with metadata indicating the WSI from which the patch was created and/or the patient associated with the WSI from which the patch was created. For example, in the training process, WSIs with microbiome levels established by other means, such as WGS or WTS in Poore et al., or by manual review, may be divided into patches.

The patches 206 may be generated automatically from one or more training WSIs 203. The input of the neural network, for training or for testing, may comprise an image patch of a particular size. The size may represent, for example, 100×100 microns which may correspond to an image patch of size 400×400 pixels for a WSI with 40× magnification. It should be appreciated any patch size and any WSI size may be used and that the numbers provided herein are provided solely as an example.

Each of the input patches 206 may also be associated with metadata indicating a microbiome level, such as a number or percentage indicating an amount of microbiome in the patch or a categorization such as microbiome-high or microbiome-low. The metadata indicating the microbiome level may be described as a ground truth microbiome label or classification.

The ground truth microbiome label may be used to train the neural network 212 to generate patch-based results. A patch-based result may comprise an indication, such as a level of confidence, that the patch is associated with one of microbiome-high or microbiome-low. In some embodiments, the neural network may be trained to output a confidence score for each of microbiome-high and microbiome-low for each input patch.

In some embodiments, multiple CNNs may be separately trained. By training different CNNs, each trained CNN 218 can be assessed separately, and a most accurate trained CNN 218 may be selected for use. In some embodiments, results from different training checkpoints from different CNNs may be aggregated. Such aggregation may result in more stable performance.

In this set, 7 patients (patient IDs 020-001, -004, -007, -009, -013, -015, and -018) had positive (dark gray in the pCR column) for malignancy response at week 12 or 27.6 of 7 non-responders were found to have an increase in microbiome-high probability with treatment.

Generating a set of training data for a system as described herein may comprise utilizing any available data. Such data may be, for example, microbiome analysis of Poore et al. using whole-genome (WGS) and whole-transcriptome sequencing (WTS) of solid tissue (i.e., not blood) samples of bladder (TCGA-BLCA; n=408) cancer. The set of training data may comprise one or more WSIs for each patient of a plurality of patients. For example, in Poore et al., each of 71.8% of the patients had one sample sequenced for microbiome while the remaining 28.2% each had between two and six samples. The readings for each of the samples associated with a respective patient may be averaged to give a mean-level per patient. The mean-levels per patient may be used to rank the patients and to partition the patients into microbiome-low or microbiome-high categories relative to the median for the entire cohort.

Categorizing patient samples into microbiome-low and microbiome-high categories may in some embodiments involve categorizing certain patients which have standard deviations crossing the median threshold that separate microbiome-low and -high patients. For example, such patients may be associated with ambiguous whole transcriptome sequencing (WTS) readings, underscoring that omics-based microbiome estimation methods have inherent noise and that microbiome levels may exhibit a continuous spectrum, rather than a clear separation into microbiome-high or -low classes. Nevertheless, a system of classifying issues based on microbiome levels as described herein provides clinical utility.

In some embodiments, the neural network 212 may be trained for a number of epochs with a starting learning rate, such as 0.1 or 0.2. For example, the neural network 212 may be initialized with a number of weights. In some embodiments, random values may be automatically used as weights. During training, input patches 206 may be fed to the neural network 212. The neural network 212 may process the patches 206 layer by layer, ultimately generating a probability distribution over the possible classes of microbiome-low and microbiome-high. Next, in some embodiments, the predicted class probabilities generated by the neural network 212 may be compared to the true labels associated with the training WSIs 203, such as by using a loss function, for example cross-entropy loss. Next, the initial weights of the neural network 212 may be updated, such as by using an optimization algorithm, for example stochastic gradient descent (SGD), based on the calculated loss. These steps may be repeated for multiple epochs until the neural network 212 converges on a constant loss. During testing, testing patch-based results 215 may be generated. Such testing patch-based results 215 may be in the form of data which may be stored in memory of a computer system 103 as illustrated in FIG. 1, a trained convolutional neural network (CNN) 218, which may be trained as discussed above in relation to neural network 212, may be used in the testing element of the ML system 200. The trained CNN 218 may be, for example, a process executed by a processor 106 of a computer system 103 as illustrated in FIG. 1. In some embodiments, the same neural network 212, once trained, may be used as the trained CNN 218. The trained CNN 218 may be a class of one or more computational models in deep learning particularly well-suited to image analysis. The trained CNN 218 may leverage a variation of multilayer perceptions which require a certain amount of preprocessing of input images, such as a WSI. It should be appreciated that the trained CNN 218 may comprise an input layer and an output layer as well as a number of other layers such as convolutional layers, pooling layers, fully connected layers, normalization layers, hidden layers, etc. In some embodiments, convolutional blocks may use shared weights, in which each input is processed in a same or analogous manner. In some embodiments, convolutional blocks may use different weights to process inputs in different manners.

Layers of the trained CNN 218 may be configured to apply a convolution operation to an input and pass a result to a next layer. Pooling layers may be utilized to reduce a dimension of the input data by combining outputs of neuron clusters at one layer into a single neuron in the next layer. In some embodiments, max pooling may use a maximum value from each neuron of a cluster of neurons at the prior layer, while in some embodiments average pooling may use an average value from each neuron.

While the embodiments described herein refer to a single CNN, it should be appreciated that a plurality of CNNs may be utilized together and may effectively form a single trained CNN 218. Also, the methods and systems described herein may be used to train a plurality of CNNs to each identify differently types of microbiomes in diverse types of WSIs, such as images of blood samples, images of tissue samples, etc., and for head and neck cancer, ovarian cancer, bladder cancer, or other types of cancers.

The input to the trained CNN 218 may comprise WSIs 221 divided into overlapping or non-overlapping patches 224. As described above, ground truth labels for each testing WSI 221 may be used for each patch 224 from the respective WSI 221. In some embodiments, a majority voting mechanism 230 may be used to aggregate patch-level results into WSI-level predicted labels for testing purposes as described below. Microbiome classification labels used for testing the trained CNN 218 may be obtained from a source, such as per patient from Poore et al., and may be used to annotate training and/or testing WSIs 203, 221 and their corresponding patches. When evaluating new WSIs 221 from a test set (using all patches 224 per test WSI 221), a majority voting mechanism 230 may be used to aggregate patch-level results 227 into WSI-level predicted labels 233 as described in greater detail below. As described herein, the probability of a test WSI 221 being a microbiome-high may be determined based on the percentage of patches 224 associated with the test WSI 221 which were classified by the trained CNN 218 as microbiome-high. Similarly, the probability of a test WSI 221 being a microbiome-low may be determined based on the percentage of patches 224 associated with the test WSI 221 which were classified by the trained CNN 218 as microbiome-low. In the test process, the patch-based results are aggregated to give an image-based probability of microbiome in the test WSI.

As described above, a trained CNN 218 may be configured to generate patch-based results 227 based on input patches 224. Input patches 224 may be generated by the trained CNN 218 automatically from one or more test WSIs 221. The patched-based results 227 may be used to generate a microbiome label 233. In some embodiments, a majority voting mechanism 230 may be utilized to generate the microbiome label 233 based on the patch-based results.

WSIs such as may be used for training and/or testing a neural network as well as for analyzing using a trained neural network may be as illustrated in FIGS. 3A-H.

Figure 3A:
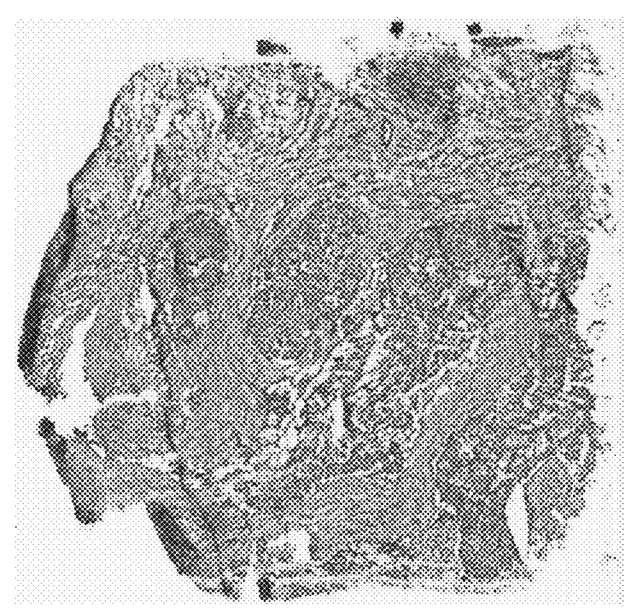
FIGS. 3A-3H are illustrative whole slide images which may be used for analysis in accordance with one or more of the embodiments described herein.

FIG. 3A is an image of a WSI captured from a patient with head and neck cancer. The patient is microbiome-low. When the image of FIG. 3A is input into a trained CNN as described herein, the trained CNN may output an indication that the WSI is microbiome-low.

Figure 3B:
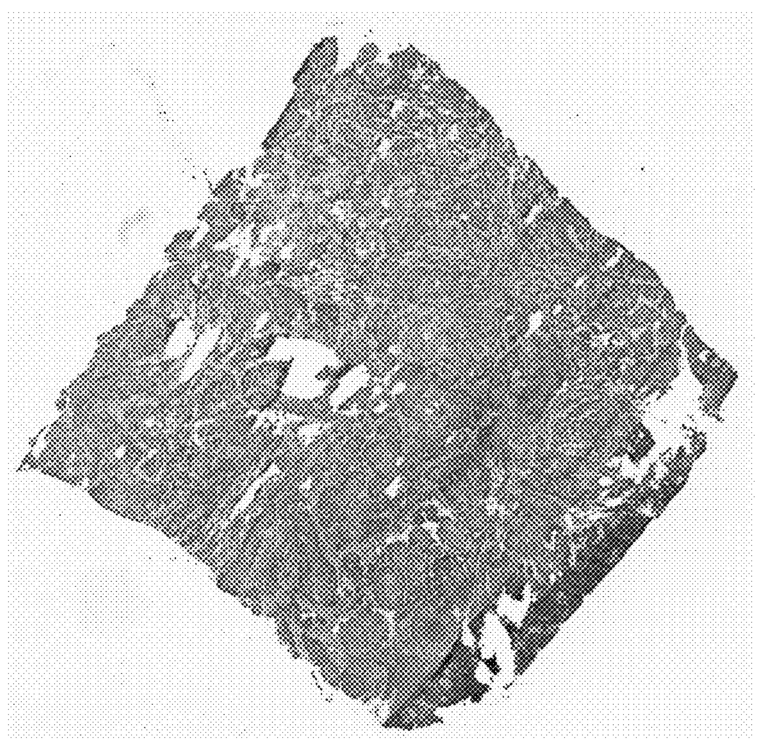

FIG. 3B is an image of a WSI captured from a patient with head and neck cancer. The patient is microbiome-high. When the image of FIG. 3B is input into a trained CNN as described herein, the trained CNN may output an indication that the WSI is microbiome-high.

Figure 3C:
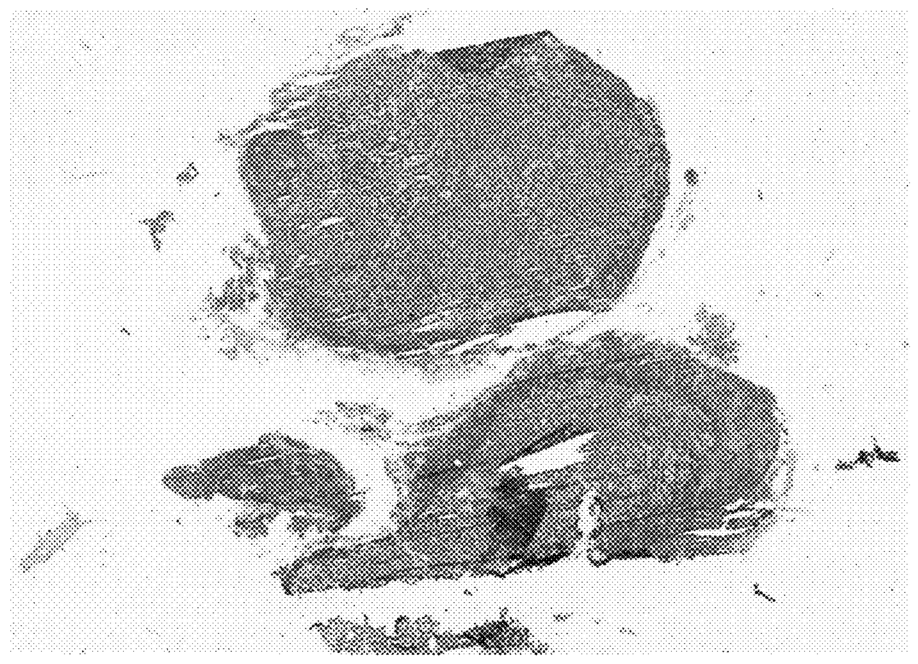

FIG. 3C is an image of a WSI captured from a patient with ovarian cancer. The patient is microbiome-low. When the image of FIG. 3C is input into a trained CNN as described herein, the trained CNN may output an indication that the WSI is microbiome-low.

Figure 3D:
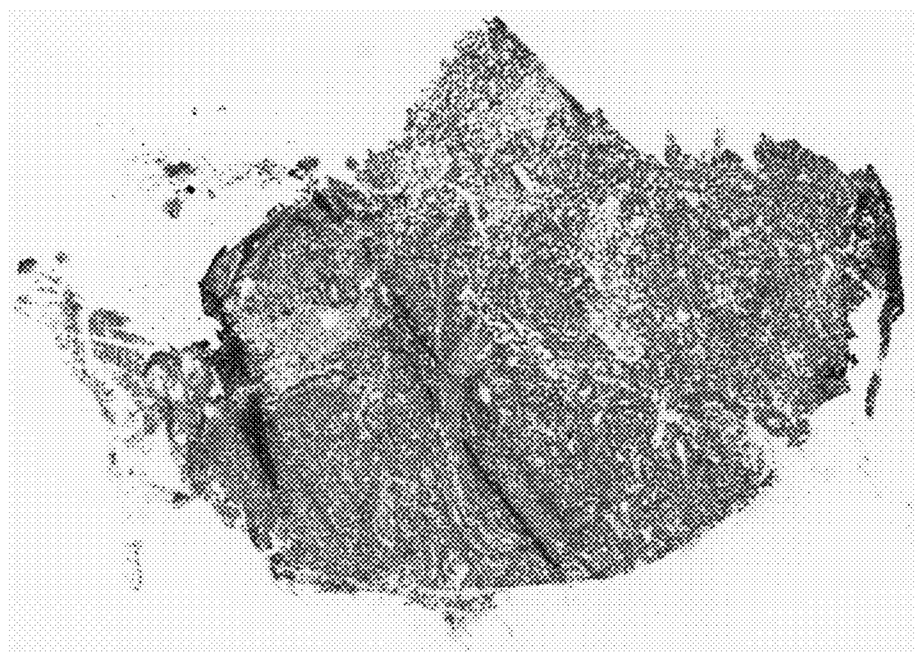

FIG. 3D is an image of a WSI captured from a patient with ovarian cancer. The patient is microbiome-high. When the image of FIG. 3D is input into a trained CNN as described herein, the trained CNN may output an indication that the WSI is microbiome-high.

Figure 3E:
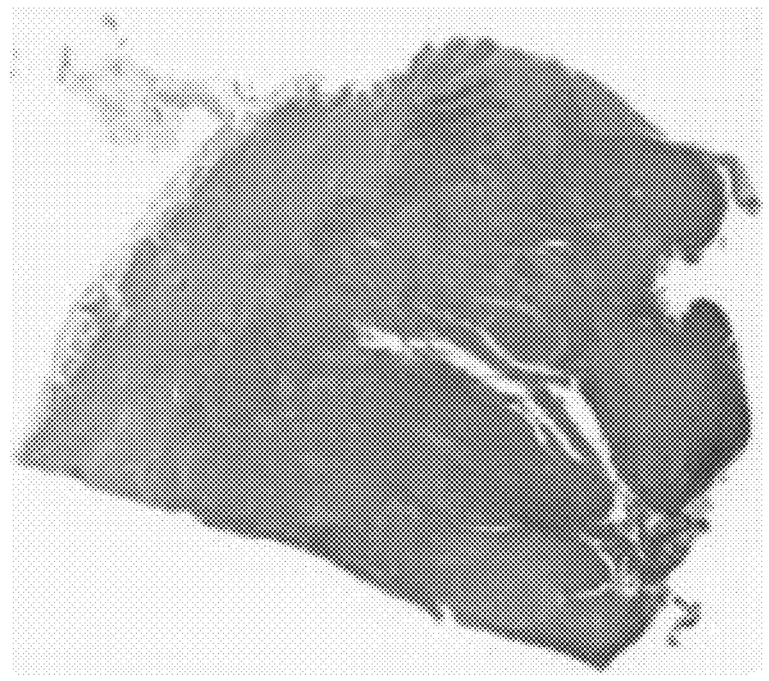
Figure 3F:
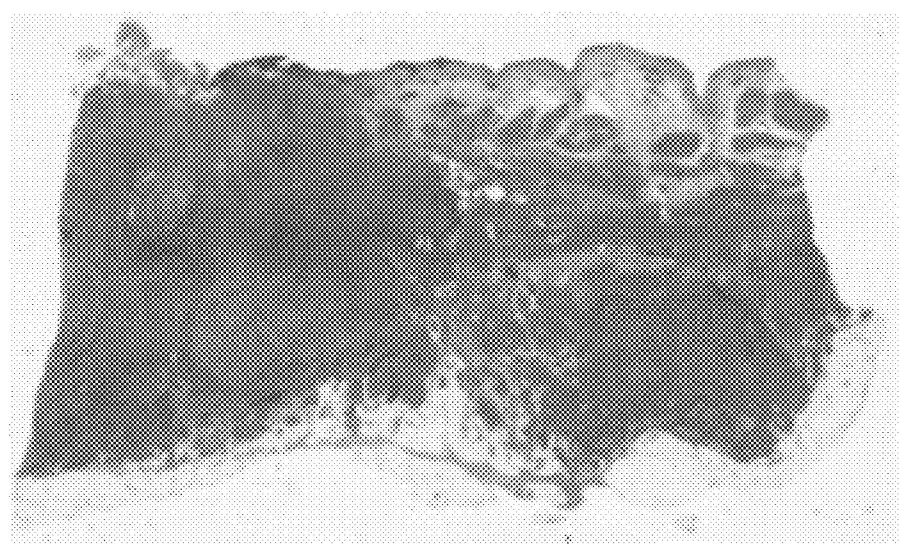
Figure 3G:
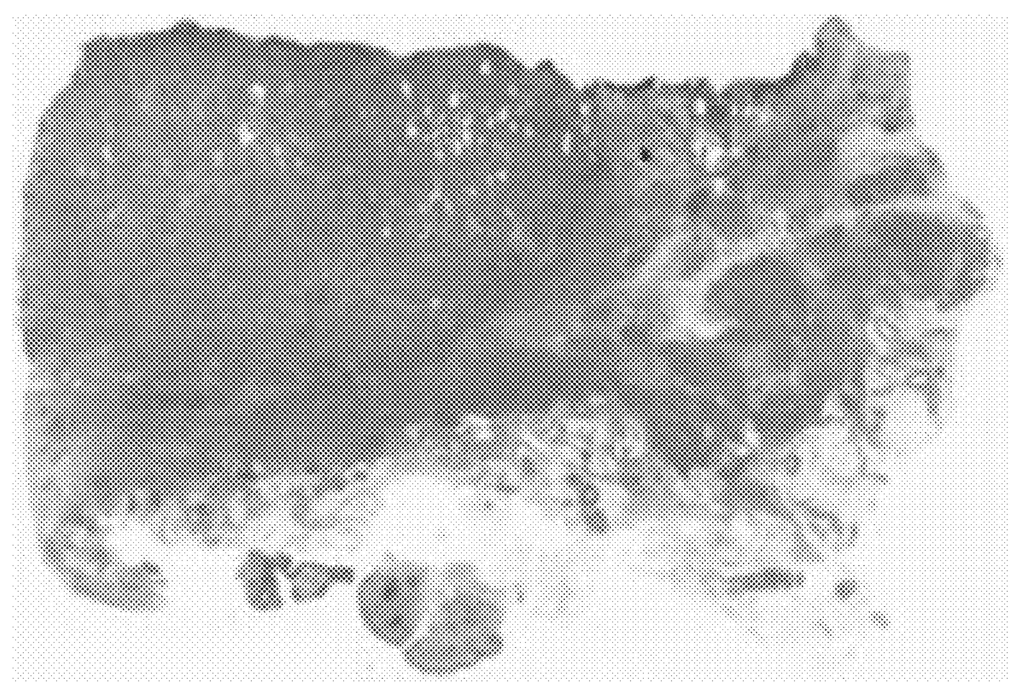
Figure 3H:
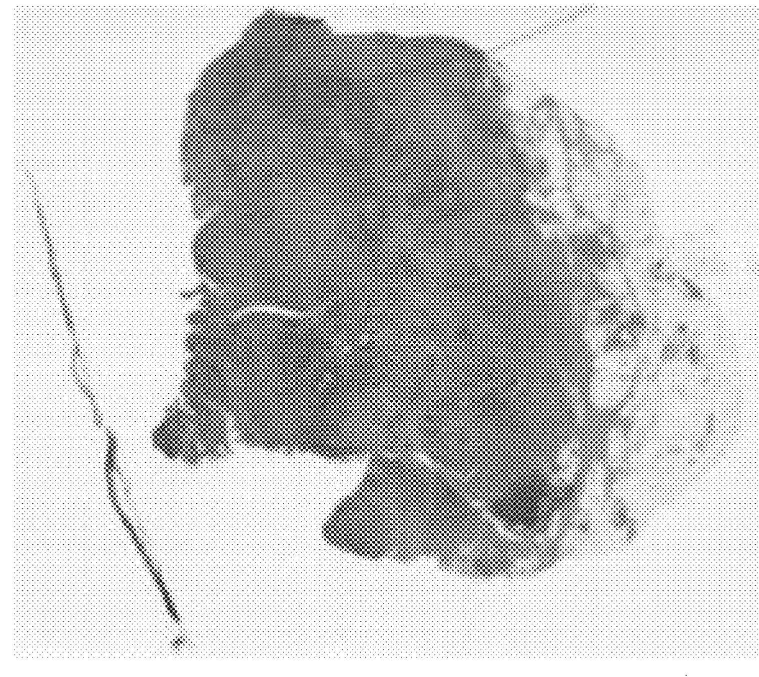

FIGS. 3E-H illustrate WSIs from TCGA bladder cancer cohort patients each of which has been classified as one of microbiome-low and microbiome-high. The test images of FIGS. 3E and 3F are microbiome-low and the test images of FIGS. 3G and 3H are microbiome-high patients.

When the WSI of FIG. 3E is input into a trained CNN 218 as described herein, the trained CNN 218 may output a probability of the tissue imaged in the WSI being microbiome-high as being nine percent and the probability of the tissue imaged in the WSI being microbiome-low as being ninety-one percent. As a result, an indication that the WSI of FIG. 3E is microbiome-low may be generated.

When the WSI of FIG. 3F is input into a trained CNN 218 as described herein, the trained CNN 218 may output a probability of the tissue imaged in the WSI being microbiome-high as being sixty-one percent and the probability of the tissue imaged in the WSI being microbiome-low as being thirty-nine percent. As a result, an indication that the WSI of FIG. 3F is microbiome-high may be generated.

When the WSI of FIG. 3G is input into a trained CNN 218 as described herein, the trained CNN 218 may output a probability of the tissue imaged in the WSI being microbiome-high as being fifteen percent and the probability of the tissue imaged in the WSI being microbiome-low as being eighty-five percent. As a result, an indication that the WSI of FIG. 3G is microbiome-low may be generated.

When the WSI of FIG. 3H is input into a trained CNN 218 as described herein, the trained CNN 218 may output a probability of the tissue imaged in the WSI being microbiome-high as being ninety-nine percent and the probability of the tissue imaged in the WSI being microbiome-low as being one percent. As a result, an indication that the WSI of FIG. 3H is microbiome-high may be generated.

Figure 4A:
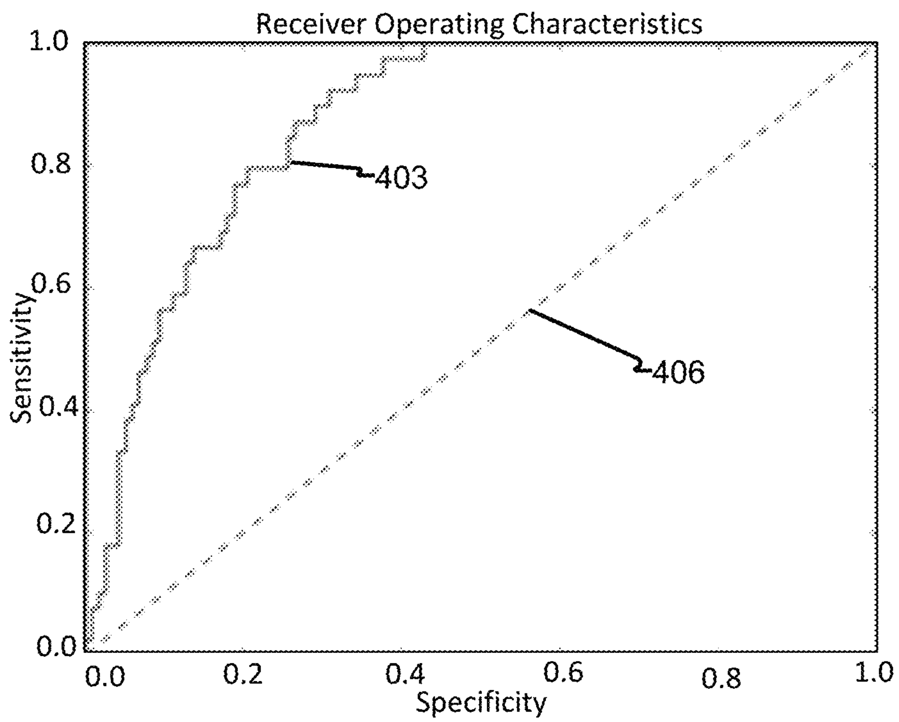
FIGS. 4A-4I are graphs showing data used with, and results of, methods and systems in accordance with one or more of the embodiments described herein.

By analyzing input images such as test WSIs 221, a computer system 103 may be enabled, using a method as described herein, of using a trained CNN 218 to identify a level or quantity of microbiome in an input image, and based on the identified microbiome in the input image, to make certain determinations relating to the microbiome and to the existence of cancer in a patient associated with the input image. Results of using a system or method as described herein are illustrated in FIGS. 4A-4I, described in detail below. FIG. 4A illustrates receiver operating characteristics for a first patient charted by sensitivity from zero to one on the vertical axis and specificity from zero to one on the horizontal axis. The curved line 403 indicates performance of a system as described herein. The straight line 406 indicates a one-to-one relationship between sensitivity and specificity. Performance of the system can be measured using an area-under-curve (AUC) for the performance of system charted by the curved line 403. An AUC closer to one indicates the system is capable of accurately determining whether an input WSI associated with the first patient is microbiome-high or microbiome-low. In the example illustrated in FIG. 4A, the AUC is 0.875.

Figure 4B:
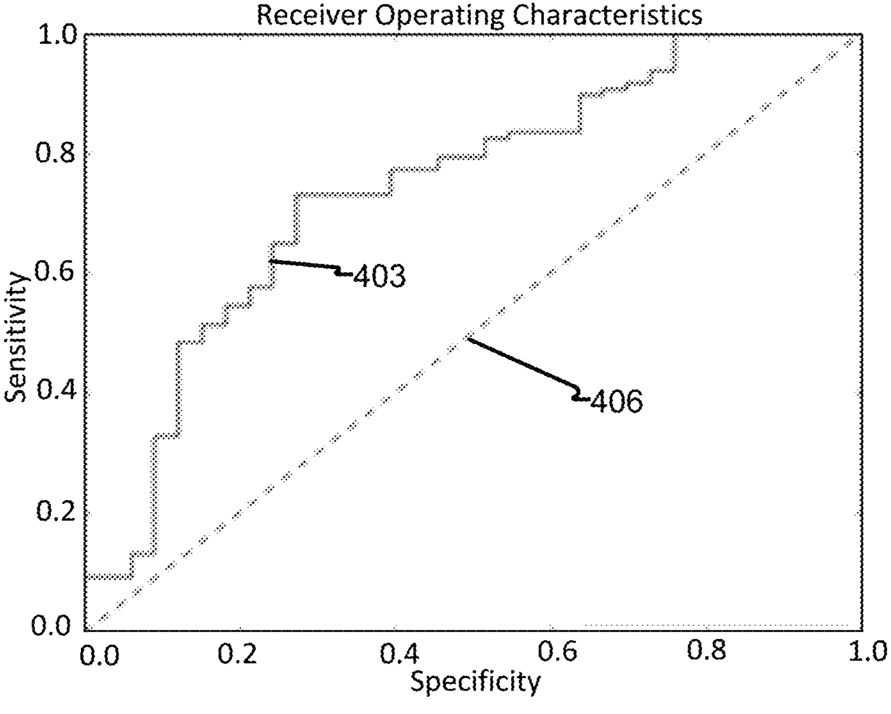

FIG. 4B illustrates receiver operating characteristics for a second patient charted by sensitivity from zero to one on the vertical axis and specificity from zero to one on the horizontal axis. The curved line 403 indicates performance of a system as described herein. The straight line 406 indicates a one-to-one relationship between sensitivity and specificity. Performance of the system can be measured using an area-under-curve (AUC) for the performance of system charted by the curved line 403. An AUC closer to one indicates the system is capable of accurately determining whether an input WSI associated with the second patient is microbiome-high or microbiome-low. In the example illustrated in FIG. 4B, the AUC is 0.7416.

Figure 4C:
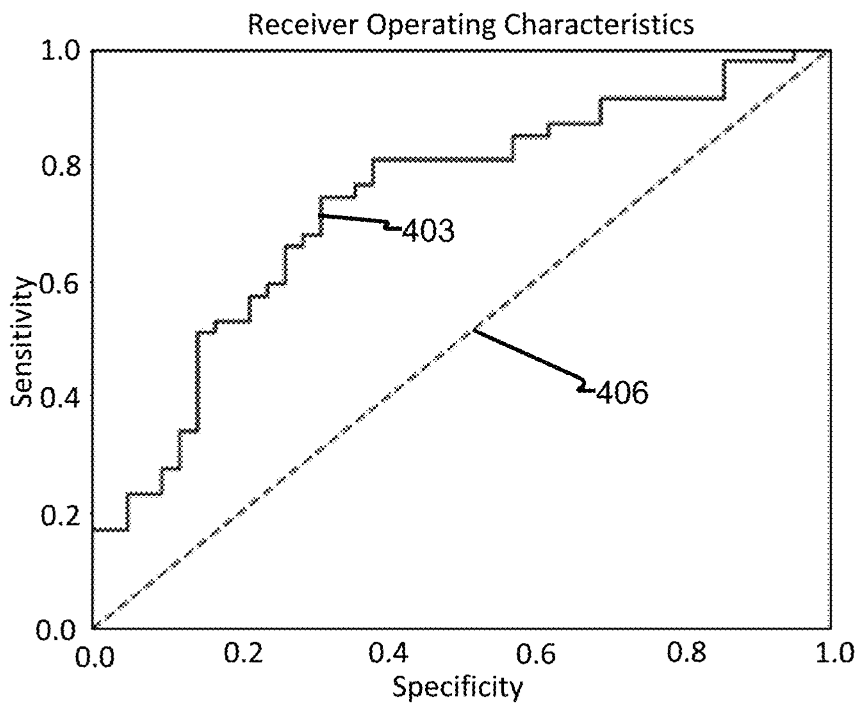
Figure 4D:
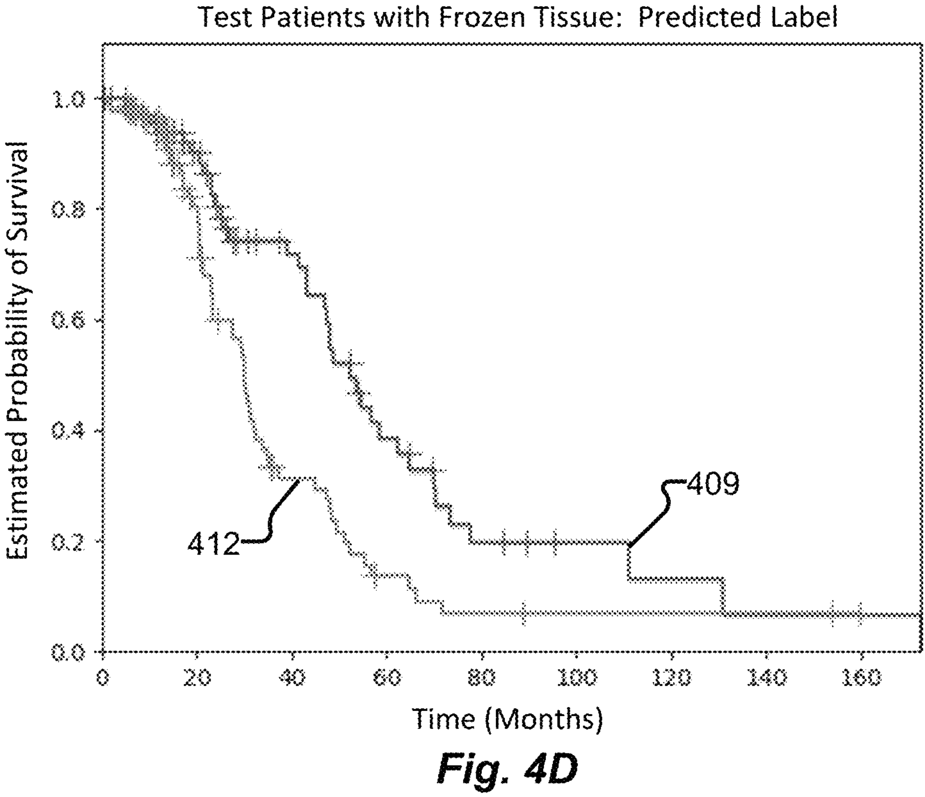
Figure 4E:
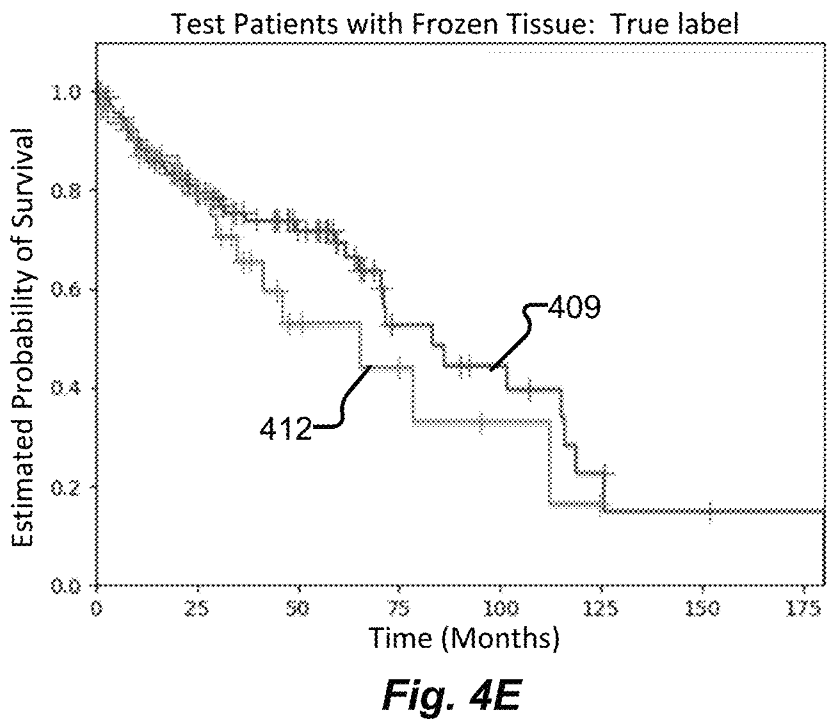
Figure 4F:
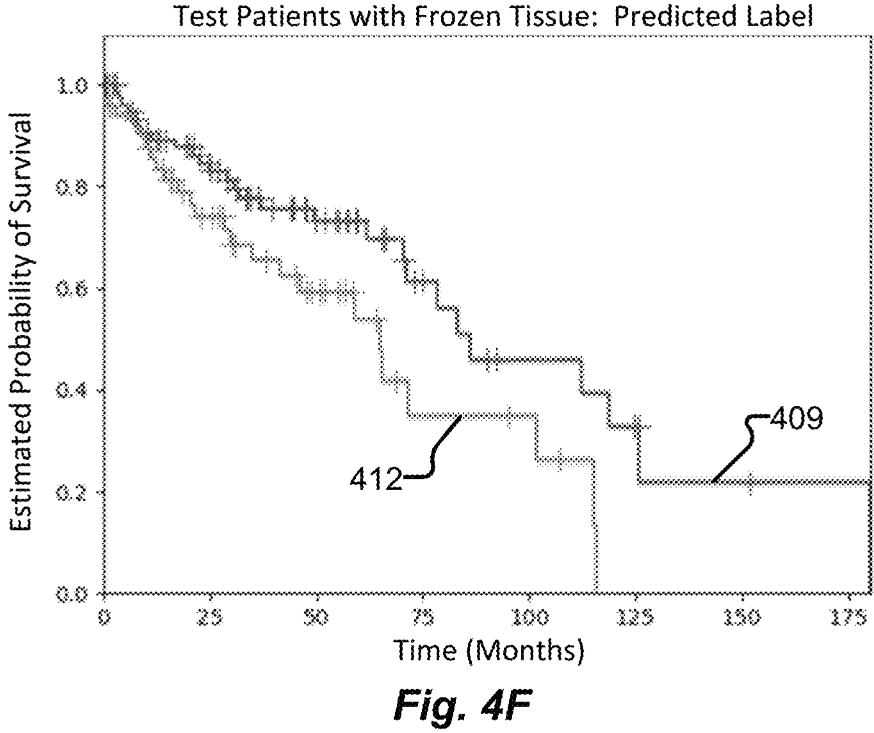
Figures 4G, 4H:
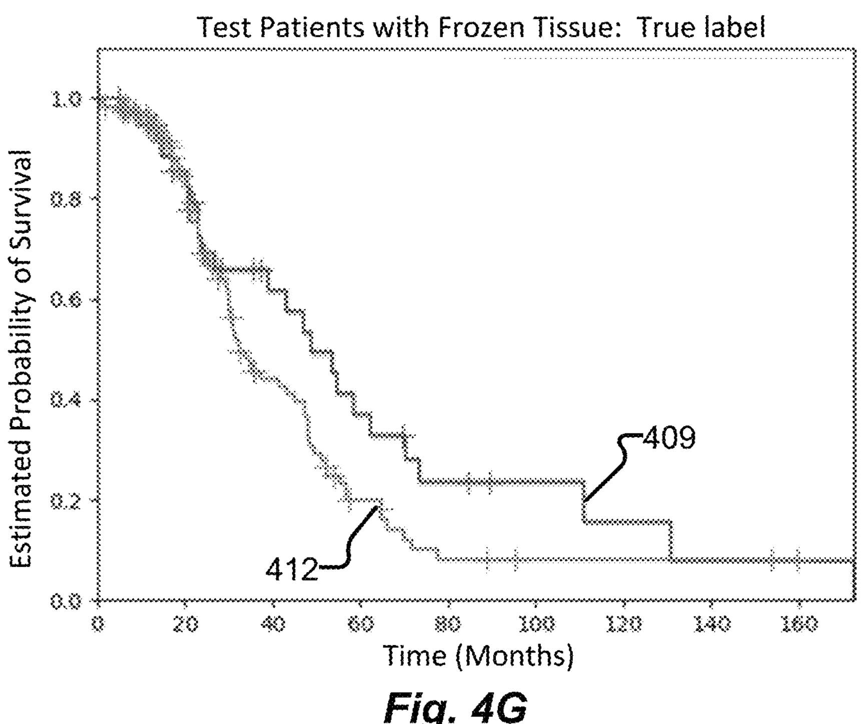
Figure 4I:
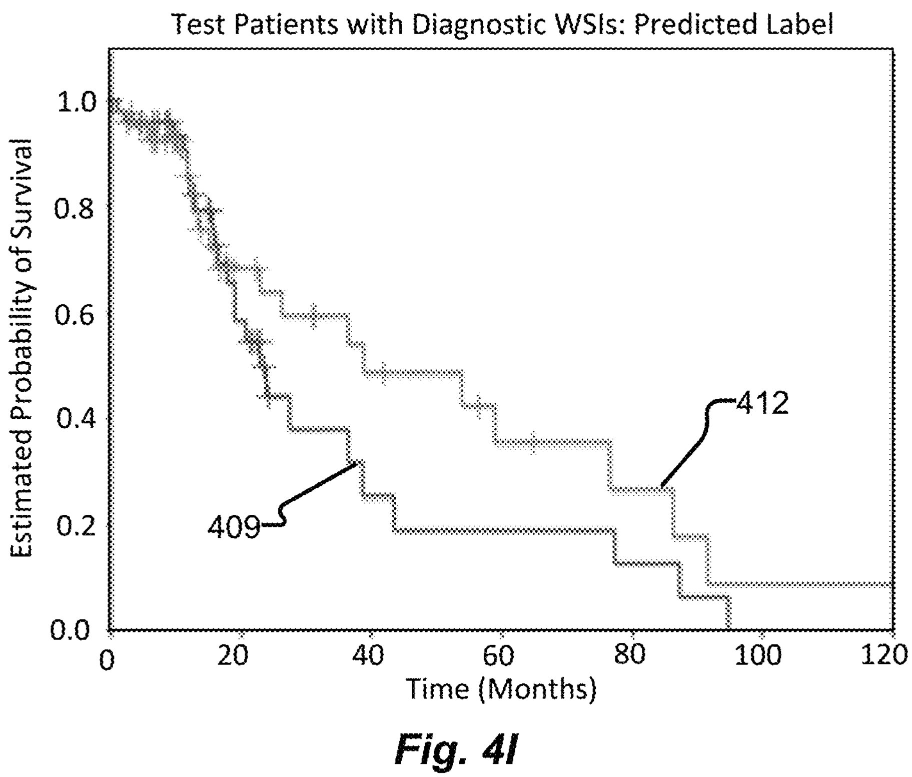

FIG. 4C illustrates receiver operating characteristics for a third patient charted by sensitivity from zero to one on the vertical axis and specificity from zero to one on the horizontal axis. The curved line 403 indicates performance of a system as described herein. The straight line 406 indicates a one-to-one relationship between sensitivity and specificity. Performance of the system can be measured using an area-under-curve (AUC) for the performance of system charted by the curved line 403. An AUC closer to one indicates the system is capable of accurately determining whether an input WSI associated with the third patient is microbiome-high or microbiome-low. In the example illustrated in FIG. 4C, the AUC is 0.7416.

Area under the ROC curve (ROC-AUC), area under the Precision-Recall curve (PR-AUC), precision, recall, and F1 score may be used as metrics to evaluate the performance of a trained CNN 218. Here, both ROC-AUC and PR-AUC look at the WSI-based prediction scores (p(microbiome-high)) of trained CNNs 218 over the entire validation or test set. Such scores may have any value from 0 to 1. However, precision, recall and F1 score values are calculated using counts of class assignments (WSIs true vs predicted microbiome-high and/or microbiome-low label) based on the optimal threshold. In some embodiments, the optimal threshold may be the one that minimizes the Euclidian distance to point (0, 1) on the ROC curve, which indicates 0% false positives and 100% true positives. All performance evaluation metrics used in this study range from zero to one, with higher values indicating better performance.

FIGS. 4D-4H illustrate examples of survival analysis of TCGA bladder test patients with ground truth labels as described above. In each illustration, an estimated probability of survival is plotted on a vertical axis and an amount of time in months is plotted on a horizontal axis. In each illustration, microbiome-high patients 409 are plotted separately from microbiome-low patients 412. As should be appreciated, microbiome-high patients generally demonstrate better outcomes in response to therapy, including higher survival over time.

Figure 5:
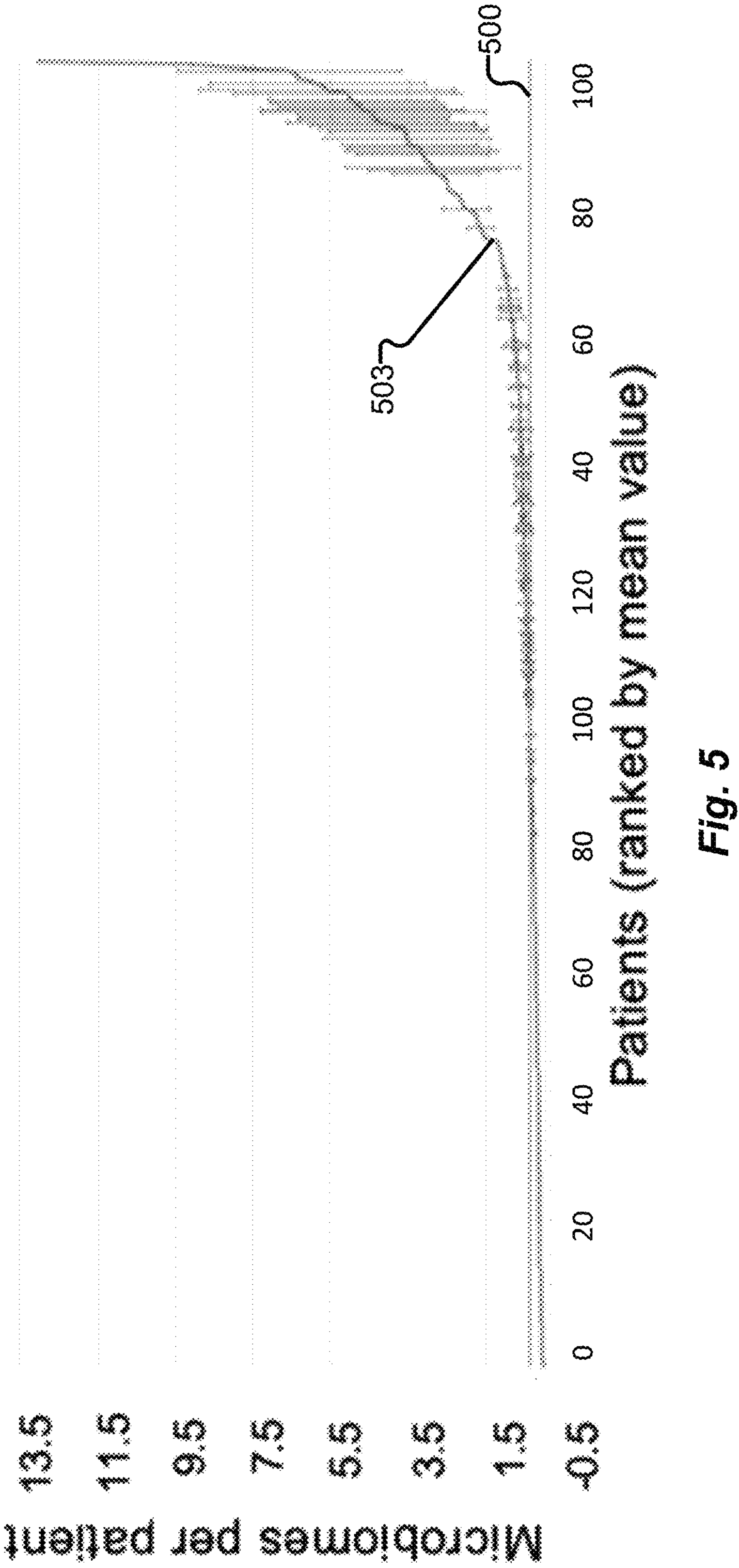
FIG. 5 is a graph illustrating microbiomes per patient in accordance with one or more of the embodiments described herein.

FIG. 5 illustrates ranked microbiome reads in TCGA cohorts using whole-genome and whole-transcriptome sequencing data. Microbiome analyses of blood and tissues suggest cancer diagnostic approach. In the graph of FIG. 5, the x axis illustrates each of the patients ranked by mean value of microbiome level. Patients to the left of the median threshold are associated with low microbiome levels and patients to the right of the median threshold are associated with high microbiome levels. The y-axis of the graph of FIG. 5 illustrates a number of microbiome reads per patient. As should be appreciated, patients with the highest levels of microbiome have a relatively high number of microbiomes. The increasing average number of microbiome levels is illustrated by the sloping line 503. A flat line 500 on the graph of FIG. 5 illustrates the median threshold, which is a patient whose microbiomes read at 391,501.50 on the y-axis. Patients below the median threshold may be categorized as microbiome-low while patients above the median threshold may be categorized as microbiome-high. As should be appreciated by the graph, 50% of the patients are indicated as microbiome-low and 50% of the patients are indicated as microbiome-high. While only two categorizations, microbiome-low and microbiome-high, are provided in the example illustrated in FIG. 5, it should be appreciated that in some embodiments, patients may be categorized into any number of groups, such as microbiome-low, microbiome-medium, microbiome-high. In the cohort of patients illustrated in FIG. 5, each patient was measured an average of 1.37 times. The median microbiome level was found to be 391,501.50.

As an example of a training, testing, and verification of a neural network as described herein for creating a trained CNN 218 capable of detecting microbiome content in WSIs associated with bladder cancer patients, a cohort of bladder cancers from the TCGA may be used. In the example, the TCGA bladder cancer cohort includes 408 patients. For training the convolutional neural network as described herein, a training set of 272 patients may be used. From the 272 patients, the TCGA includes an average of around 1 WSIs per patient, for a total of 296 WSIs. Each WSI may be divided into an average of 25,265.80 patches, for a total of 7,478,677 patches. In this example, for training, 1,024 patches per WSI may be used, leaving a total number of 303,104 patches used for training.

While the image-based microbiome-level detection system described herein uses labels informed by sequencing data, it should be appreciated that in some embodiments the system may be used to determine if sequencing is needed, such as for new patients. Because data used for analysis, such as the TCGA data, may include information about genomics relative to phenotype information, a system as described herein may also be trained on data relating to phenotype information, such as the actual structure and/or nature of the tissue, cell size and/or shape. Such a system may be trained to provide results of genomic analyses. As a result, once such a system is trained, the system can be enabled to observe a tissue phenotypic nature and provide a likelihood of the tissue including mutations which may be discovered by sequencing.

For validation purposes, thirty-four patients of the cohort may be designated, with thirty-four WSIs divided into a total of 859,037 patches. Each of the 859,037 patches may be used for validation purposes.

For testing purposes, one-hundred and two patients of the cohort may be designated for testing purposes. Ninety-nine diagnostic WSIs may be obtained from the test set, providing 2,501,314 patches. Each of the 2,501,314 patches may be used for testing purposes.

Each of the numbers provided herein are provided solely for examples and should not be considered as limiting in any way.

Figure 6B:
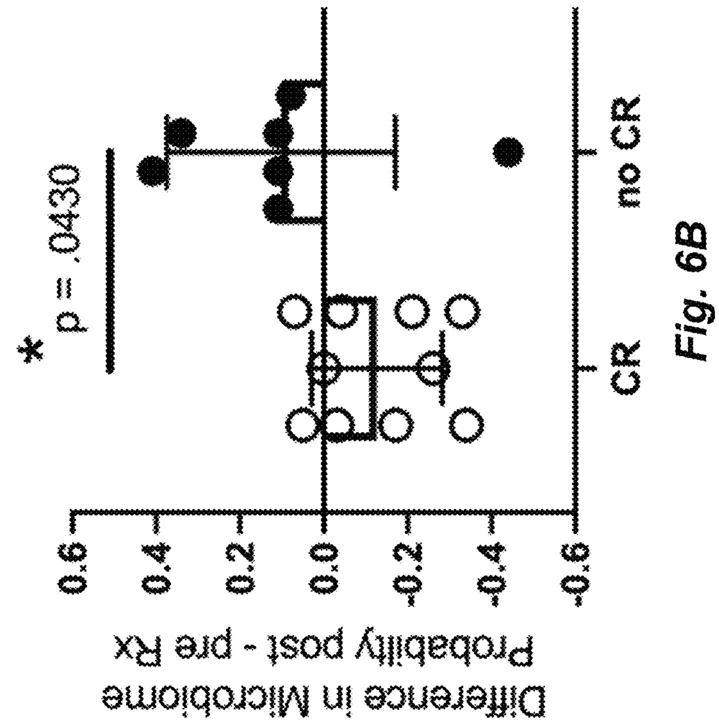
FIGS. 6A and 6B are graphs illustrating microbiome probability in accordance with one or more of the embodiments described herein.
Figure 6A:
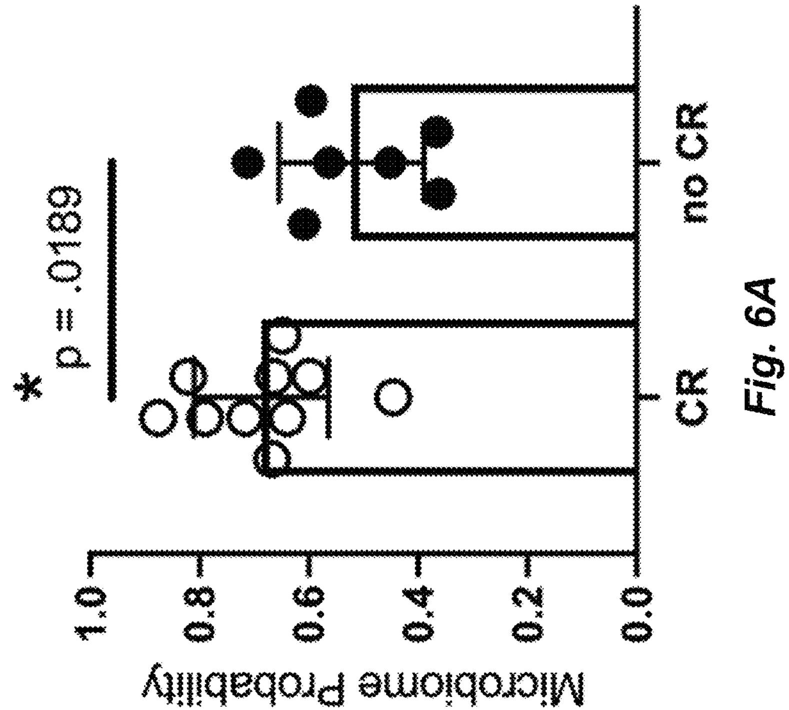

FIGS. 6A and 6B illustrate image-based microbiome detection and response to therapy in a clinical trial. In FIG. 6A, the correlation between microbiome-high probability and probability of a complete response (CR) at the time of screening is illustrated. In FIG. 6B, the correlation between microbiome-high probability and probability of CR after screening, such as 12-27 weeks after screening, is illustrated.

Figure 7:
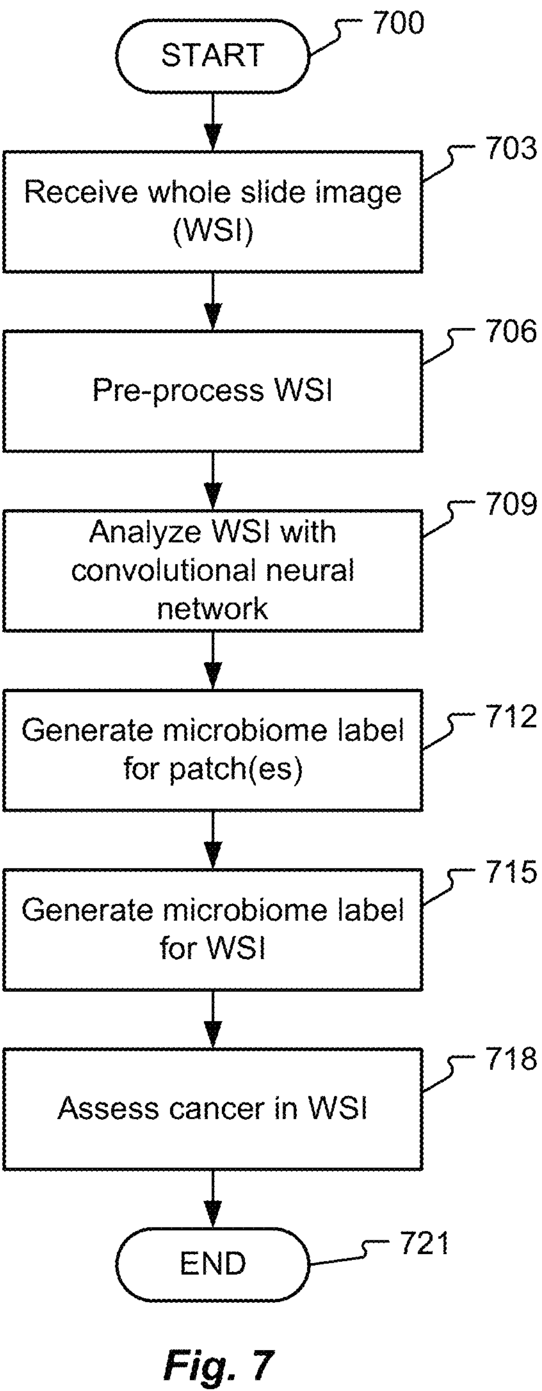
FIG. 7 is a flowchart of a method in accordance with one or more of the embodiments described herein.

Once a CNN is tested and trained using a system 200 as described above, a computer system 103, as illustrated in FIGS. 1 and 2, may be used to perform a method of classifying new WSIs with microbiome labels. Such a method may be as illustrated by the flowchart of FIG. 7 and may begin at 700 in which the computer system 103 may initiate a trained CNN 218. The trained CNN may be trained using a training and testing system as illustrated in FIG. 2. The trained CNN may be a process executed by a processor 106 of the computer system 103.

At 703, the computer system 103 may receive raw input data. Raw input data may be, for example, a WSI as described herein, and such as illustrated in FIGS. 3A-3H. The raw input data may be received via a network such as illustrated in FIG. 1. The computer system 103 may be capable of receiving multiple WSIs. Each WSI may be related to the same or different patients. For example, two or more WSIs may each relate to the same patient. Each WSI may include or be associated with metadata describing the patient with which the WSI is related and/or other information. The computer system 103 may also or alternatively be capable of receiving patches created from WSIs. For example, another system may be used to divide a WSI into patches. As described below, in step 706, an input WSI may be divided by the computer system 103 into patches.

At 706, the input data, whether one or more WSIs or one or more patches, may be preprocessed by the computer system 103 to be used as an input to a trained CNN 218 such as illustrated in FIG. 2. Pre-processing the input may be automatic, i.e., no human interaction required. Pre-processing may comprise one or more of adjusting image quality, contrast, size, brightness, orientation, etc. Pre-processing may also comprise dividing an input WSI into a plurality of patches as described herein. In some embodiments, a single WSI may be divided into any number of patches. As an example, and not to be considered as limiting in any way, each WSI may be divided into over 25,000 patches. Each patch created from a WSI may represent, for example, an area of 100 $\mu m^2$.

At 709, the processed input data may be fed as an input to the trained CNN 218 as discussed above in relation to FIG. 2. For example, each patch of the plurality of patches may be fed individually to the trained CNN 218 as an input. Based on the input, the trained CNN 218 may perform an analysis and generate an output.

Analyzing a WSI with a CNN may comprise separately analyzing a plurality of patches associated with the WSI separately with the CNN. Analyzing a patch with a trained CNN 218 may comprise an input layer of the trained CNN 218 taking the patch feeding the patch into a neural network. A series of convolutional layers of the CNN 218 may then apply a set of filters (or kernels) to the input patch or the output of the previous layer, creating feature maps that represent higher-level features in the patch. The filters are convolved across the input image or feature maps, capturing local patterns and spatial information.

The CNN 218 may use pooling layers to reduce the spatial dimensions of the feature maps. Pooling layers of the CNN 218 may utilize one or more pooling techniques such as max-pooling and average pooling. The CNN 218 may also use fully connected layers to combine the learned features and generate a final output. An output layer of the CNN 218 may be configured to generate a probability distribution over classes of microbiome-low and microbiome-high for the input patch.

At 712, the output of the trained CNN 218 may be received by the computing system. In some embodiments, an output of the trained CNN 218 may be a microbiome label indicating whether the patch or the WSI is microbiome-low or microbiome-high. For example, the trained CNN 218 may be configured to output a patch-based result, such as a microbiome label, for each patch created from a particular WSI. As such, a separate output may be created by the trained CNN 218 for each patch of the plurality of patches fed as an input.

At 715, the output of the AI may be post-processed. Post-processing may comprise determining a microbiome label for the input WSI based on each microbiome label output for each patch of the plurality of patches. The microbiome label for an input image may comprise an aggregation of each microbiome label for each of the plurality of patches.

In some embodiments, the aggregation may comprise performing or executing a majority voting mechanism. Aggregation may alternatively be implemented by averaging probabilities, computing a standard deviation, and defining predictions as ambiguous if the standard deviation around the average probability values overlaps the determined optimal classification threshold. The microbiome label may be determined based on an aggregation of results of processing a plurality of patches from the received image. In some embodiments, a majority voting mechanism 230 as illustrated in FIG. 2 may be used to aggregate the patch-level results generated by the trained CNN 218 into WSI-level predicted labels for testing purposes as described below.

At 718, the post-processed output of the AI may be used to determine a level or amount of cancer in the input image data. In some embodiments, a determination may be made as to whether the WSI contains any level of microbiome. In response to determining the image contains a high level of microbiomes, a high microbiome label may be assigned to the WSI. In response to determining the image contains no level of microbiomes, a low microbiome label may be assigned to the image.

The microbiome label may be an identification of microbial signatures in tissue and/or blood found by the CNN in the input image data. Based on the microbiome label, the computer system may be configured to automatically diagnose the patient with one or more of head and neck cancer, ovarian cancer, and bladder cancer.

In some embodiments, the output of the CNN may be compared to a previous level of cancer for the patient associated with the WSI. For example, the computer system may be configured to determine a rate of growth/shrinkage, or to determine an efficacy of a treatment or the instant patient or for a large number of patients.

Based on the output of the CNN, the computer system may be configured to determine an estimated survival, a diagnosis, and/or a treatment or prescription, for the patient associated with the WSI. In some embodiments, based on the output of the CNN, the computer system may be configured to compare different treatments for different patients over time. At 521, the method may end.

A system or method as described herein may be used in a number of ways. In some embodiments, the systems and methods described herein may be used in the context of drug trials. For example, using a system as described herein, results generated by a CNN may be automatically displayed on graphical user interfaces which may be updated in real-time with new results. Such a system may enable a single lab with any number of patients around the world to share results with patients and doctors simultaneously.

In one or more of the embodiments described herein, a system may be used for patient monitoring. For example, based on results from the CNN, real-time notifications may be transmitted to doctors and/or patients based on results from the CNN. Patients can be imaged at a local clinic and the image data can be transmitted to the lab remotely, without requiring patients to travel to any particular lab. In this way, patients may not be required to make an appointment with a radiologist or expert physician, saving time and money. A system as described herein may be used for administering a treatment to the patient based on a diagnosis created using the CNN. Diagnosing the patient may comprise, for example, calculating a likelihood of head and neck cancer, ovarian cancer, and bladder cancer for the patient.

The systems and methods described herein may be used to implement a patch-based microbiome detection system. The systems and methods may be used to classify one or more patches of a frozen tissue image, and to aggregate the patch-based results to label the frozen tissue image. If a patient is associated with multiple WSIs, each result may be aggregated to yield a single patient-level label.

As described herein, an AI-driven image-based microbiome analysis may reveal a correlation between higher pre-treatment microbiome levels and complete response in trial patients. Because the human microbiome exerts a profound influence on cancer development, progression, and response to treatment, the existence and level of microbiome in H&E-stained slides as described herein may be used to determine a level or severity of cancer in a patient as well as predict a survival rate for the patient.

An AI-driven computational pathology system as described herein may be configured to determine relative microbiome levels in H&E-stained slides. The system may further be configured to categorize WSIs as microbiome-low or microbiome-high.

The system as described herein may be trained using FFPE diagnostic (DX) images from TCGA bladder cancer cohort (n=408). The system may be used to determine a correlation between TCGA bladder cancer patient survival and microbiome level.

The system as described herein may be used to analyze pathologic complete response (pCR) and microbiome level in non-muscle invasive bladder cancer patients in patient trials.

Using a system as described herein, a computational tumor-tissue-specific image-based microbiome level detector may be developed for bladder cancer. The performance of the microbiome level detector for H&E stained FFPE tissues suggests the morphological alterations that the microbiome introduces to solid tumor tissue is visible to AI image systems. While the morphological alterations are too fine to be readily seen by human eye, even by a trained pathologist, the alterations are detectable to the developed AI-based image system as described herein. Using a system as described herein to perform an analysis of a relationship between survival and microbiome load in TCGA bladder patients, survival was seen to be prolonged in those with microbiome-low tumors.

Further, using a system as described herein, correlations between pathologic complete response (pCR) at 12 or 27 weeks and microbiome level in non-muscle invasive bladder cancer patients in a clinical trial may be assessed. Patients that achieved a pCR with treatment were found to have significantly higher probability of microbiome-high pre-treatment, as compared to those who did not achieve a pCR. Reductions in predicted microbiome levels after treatment may also be observed in pCR patients. Conversely, 6 of 7 non-responders were found to have an increase in microbiome-high probability with treatment. Such findings suggest the novel AI-driven image-based computational pathology system as described herein has the potential to provide data that may not only inform clinical decision-making, but also allow further investigation into the role of the TME microbiome in cancer.

A patient's response to a cancer treatment can be assessed with the systems and methods and/or uses described herein at more than one time point. For example, the response to treatment can be assessed at times of about 1 week, 2 weeks, 3 weeks, 4 weeks, 1 month, 2 months, 3 months, 4 months, 5 months, 6 months, 7 months, 8 months, 9 months, 10 months, 11 months, 12 months, 13 months, 15 months, 18 months, 2 years, 3 years, 4 years or more apart.

In addition, a patient's response to a cancer treatment can be assessed at various time points before or during treatment. In certain embodiments, a level of microbiomes is determined as disclosed herein prior to or before the patient is administered a cancer treatment. This level is then compared to a level of microbiomes that are determined as disclosed herein following or after administration of the cancer treatment to the patient. The level of microbiomes can be assessed at times of about 1 week, 2 weeks, 3 weeks, 4 weeks, 1 month, 2 months, 3 months, 4 months, 5 months, 6 months, 7 months, 8 months, 9 months, 10 months, 11 months, 12 months, 13 months, 15 months, 18 months, 2 years, 3 years, 4 years, or more after the cancer treatment initiation.

In certain embodiments, the patient's response to a cancer treatment can be assessed after initiation of the cancer treatment, for example to evaluate or assess the effectiveness of the cancer treatment. For example, the patient's response to a cancer treatment can be assessed as disclosed herein before initiation of a cancer treatment and then again at a second time point after initiation of the cancer treatment. One can then compare the level of microbiomes determined by the methods and/or uses disclosed herein to a cancer treatment efficacy. The cancer treatment efficacy evaluation can then be used to decide whether to continue or discontinue the cancer treatment. In another example, the patient's response to a cancer treatment can be assessed at one timepoint after the cancer treatment and then again at one or more additional timepoints following additional rounds of the cancer treatment. One can then compare the level of microbiomes at each time point determined by the methods and/or uses disclosed herein. The cancer treatment efficacy evaluation can then be used to decide whether to continue or discontinue the cancer treatment.

In one aspect, the patient has not received the cancer treatment. In another aspect, the patient has received the cancer treatment for some duration of time.

The phrases "cancer therapy" or "anti-cancer therapy" are used interchangeably to convey a therapy useful in treating cancer. Examples of anti-cancer therapeutic agents include, but are not limited to surgery, chemotherapeutic agents, immunotherapy, growth inhibitory agents, cytotoxic agents, radiation therapy, anti-angiogenic agents, apoptotic agents, anti-tubulin agents, and other agents to treat cancer, such as anti-HER-2 antibodies (e.g., HERCEPTIN™), anti-CD20 antibodies, an epidermal growth factor receptor (EGFR) antagonist (e.g., a tyrosine kinase inhibitor), HER1/EGFR inhibitor (e.g., erlotinib (TARCEVA™)), platelet derived growth factor inhibitors (e.g., GLEEVEC™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations of these therapies and therapeutic agents are also contemplated for use within the methods described herein.

A "chemotherapeutic agent" is a chemical compound useful in the treatment of cancer. Examples of chemotherapeutic agents include Erlotinib (TARCEVA™, Genentech/OSI Pharm.), Bortezomib (VELCADE™, Millennium Pharm.), Fulvestrant (FASLODEX™, Astrazeneca), Sutent (SU11248, Pfizer), Letrozole (FEMARA™, Novartis), Imatinib mesylate (GLEEVEC™, Novartis), PTK787/ZK 222584 (Novartis), Oxaliplatin (Eloxatin™, Sanofi), 5-FU (5-fluorouracil), Leucovorin, Rapamycin (Sirolimus, RAPAMUNE™, Wyeth), Lapatinib (GSK572016, GlaxoSmithKline), Lonafarnib (SCH 66336), Sorafenib (BAY43-9006, Bayer Labs.), and Gefitinib (IRESSA™, Astrazeneca), AG1478, AG1571 (SU 5271; Sugen), alkylating agents such as Thiotepa and CYTOXAN™ cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozcicsin, carzcicsin and bizcicsin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin yl and calicheamicin omega 1 (*Angew Chem. Intl. Ed. Engl.* (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, anthramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN™ doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, strcptonigrin, strcptozocin, tubcrcidin, ubenimcx, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacytidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK™ polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosinc; arabinoside ("Ara-C"); cyclophosphamidc; thiotcpa; taxoids, e.g., TAXOL' paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE™ doxetaxel (Rhone-Poulenc Rorer, Antony, France); chloranbucil; GEMZAR™ gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE™ vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above.

Also included in this definition of "chemotherapeutic agent" are: (i) anti-hormonal agents that regulate or inhibit hormone action on tumors such as anti-estrogens and selective estrogen receptor modulators (SERMs), including, for example, tamoxifen (including NOLVADEX™ (tamoxifen)), raloxifene, droloxifene, 4-hydroxytamoxifen, trioxifene, keoxifene, LY117018, onapristone, and FARESTON™ (toremifene); (ii) aromatase inhibitors that inhibit the enzyme aromatase, which regulates estrogen production in the adrenal glands, such as, for example, 4(5)-imidazoles, aminoglutethimide, MEGASE™ (megestrol acetate), AROMASIN™ (exemestane), formestanie, fadrozole, RIVISOR™ (vorozole), FEMARA™ (letrozole), and ARIMIDEX™ (anastrozole); (iii) anti-androgens such as flutamide, nilutamide, bicalutamide, leuprolide, and goserelin; as well as troxacitabine (a 1,3-dioxolane nucleoside cytosine analog); (iv) aromatase inhibitors; (v) protein kinase inhibitors; (vi) lipid kinase inhibitors; (vii) antisense oligonucleotides, particularly those which inhibit expression of genes in signaling pathways implicated in aberrant cell proliferation, such as, for example, PKC-alpha, Ralf and H-Ras; (viii) ribozymes such as a VEGF expression inhibitor (e.g., ANGIOZYIVIE™ (ribozyme)) and a HER2 expression inhibitor; (ix) vaccines such as gene therapy vaccines, for example, ALLOVECTIN™ vaccine, LEUVECTIN™ vaccine, and VAXID™ vaccine; PROLEUKIN™ rIL-2; LURTOTECAN™ topoisomerase 1 inhibitor; ABARELIX™ rmRH; (x) anti-angiogenic agents such as bevacizumab (AVASTIN™, Genentech); and (xi) pharmaceutically acceptable salts, acids or derivatives of any of the above.

Treatment of cancer patients may include any of the following: adjuvant therapy (also called adjunct therapy or adjunctive therapy) to destroy residual tumor cells that may be present after the known tumor is removed by the initial therapy (e.g. surgery), thereby preventing possible cancer reoccurrence; neoadjuvant therapy given prior to the surgical procedure to shrink the cancer; induction therapy to cause a remission, typically for acute leukemia; consolidation therapy (also called intensification therapy) given once a remission is achieved to sustain the remission; maintenance therapy given in lower or less frequent doses to assist in prolonging a remission; first line therapy (also called standard therapy); second (or 3rd, 4th, etc.) line therapy (also called salvage therapy) is given if a disease has not responded or reoccurred after first line therapy.

As used herein, "tumor" means a mass of transformed cells engaged in neoplastic uncontrolled cell multiplication and, at least in part, containing angiogenic vasculature. Abnormal neoplastic cell growth is rapid and continues even after the stimuli that initiated the new growth have ceased. "Tumor" is used broadly to include the tumor parenchymal cells as well as the supporting stroma, including the angiogenic blood vessels that infiltrate the tumor parenchymal cell mass. Although a tumor generally is a malignant tumor, i.e., a cancer having the ability to metastasize (i.e., a metastatic tumor), a tumor also can be nonmalignant (i.e., non-metastatic tumor).

"Patient" or "individual" or "subject" are used interchangeably herein, and refer to a mammalian subject to be treated, typically a human patient.

The systems and methods described herein may also be extended in other ways. For example, instead of modeling the problem as a classification problem and predicting a label, the problem may be modeled as a regression task where the goal may be to predict microbiome quantity in pathology images.

Furthermore, a cancer may be rich with several microbial signatures. In the future, the number of microbiomes per cancer may be studied separately from images. Thus, instead of starting with one binary true label (microbiome-high vs. microbiome-low), a microbiome specific analysis may be performed, such as whether microbiome X appears or does not appear in image data, or some combination thereof. Such analysis may be used to determine an optimal microbiome environment for immune stimulation.

Still further, the systems and methods and/or uses disclosed herein can further comprise integration of supplementary data to augment the images associated with the patient (i.e., the pathology slides). Such supplementary data can be obtained for example from RNA sequencing (RNA-seq). Further, for example, the supplementary data can be from a vector consisting of several transcript expression levels that can be processed as a parallel input into a neural network that may encode complementary information that may improve the system's accuracy or ability to generalize across patient samples, tissues, and cancer types.

Any of the steps, functions, and operations discussed herein can be performed continuously and automatically.

The exemplary systems and methods and/or uses of this invention have been described in relation to head and neck cancer, ovarian cancer, and bladder cancer and components and methods for analyzing and determining the existence of microbiomes in WSIs. However, to avoid unnecessarily obscuring the present invention, the preceding description omits a number of known structures and devices. This omission is not to be construed as a limitation of the scope of the claimed invention. Specific details are set forth to provide an understanding of the present invention. It should, however, be appreciated that the present invention may be practiced in a variety of ways beyond the specific detail set forth herein.

Furthermore, while the exemplary embodiments illustrated herein show the various components of the system collocated, certain components of the system can be located remotely, at distant portions of a distributed network, such as a LAN and/or the Internet, or within a dedicated system. Thus, it should be appreciated, that the components or portions thereof (e.g., microprocessors, memory/storage, interfaces, etc.) of the system can be combined into one or more devices, such as a server, servers, computer, computing device, terminal, "cloud" or other distributed processing, or collocated on a particular node of a distributed network, such as an analog and/or digital telecommunications network, a packet-switched network, or a circuit-switched network. In another embodiment, the components may be physical or logically distributed across a plurality of components (e.g., a microprocessor may comprise a first microprocessor on one component and a second microprocessor on another component, each performing a portion of a shared task and/or an allocated task). It will be appreciated from the preceding description, and for reasons of computational efficiency, that the components of the system can be arranged at any location within a distributed network of components without affecting the operation of the system. For example, the various components can be located in a switch such as a PBX and media server, gateway, in one or more communications devices, at one or more users' premises, or some combination thereof. Similarly, one or more functional portions of the system could be distributed between a telecommunications device(s) and an associated computing device.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire, and fiber optics, and may take the form of acoustic or light waves, such as those generated during radio-wave and infra-red data communications.

Also, while the flowcharts have been discussed and illustrated in relation to a particular sequence of events, it should be appreciated that changes, additions, and omissions to this sequence can occur without materially affecting the operation of the invention.

A number of variations and modifications of the invention can be used. It would be possible to provide for some features of the invention without providing others.

In yet another embodiment, the systems and methods and/or uses of this invention can be implemented in conjunction with a special purpose computer, a programmed microprocessor or microcontroller and peripheral integrated circuit element(s), an ASIC or other integrated circuit, a digital signal microprocessor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this invention. Exemplary hardware that can be used for the present invention includes computers, handheld devices, telephones (e.g., cellular, Internet enabled, digital, analog, hybrids, and others), and other hardware known in the art. Some of these devices include microprocessors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein as provided by one or more processing components.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this invention is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this invention can be implemented as a program embedded on a personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Embodiments herein comprising software are executed, or stored for subsequent execution, by one or more microprocessors and are executed as executable code. The executable code being selected to execute instructions that comprise the particular embodiment. The instructions executed being a constrained set of instructions selected from the discrete set of native instructions understood by the microprocessor and, prior to execution, committed to microprocessor-accessible memory. In another embodiment, human-readable "source code" software, prior to execution by the one or more microprocessors, is first converted to system software to comprise a platform (e.g., computer, microprocessor, database, etc.) specific set of instructions selected from the platform's native instruction set.

A neural network, as described herein may comprise layers of logical nodes having an input and an output. If an output is below a self-determined threshold level, the output may be omitted (i.e., the inputs may be within an inactive response portion of a scale and provide no output), if an output is above the threshold, the output may be provided (i.e., the inputs may be within the active response portion of the scale and provide the output). The particular placement of active and inactive delineation may be provided as a step or steps. Multiple inputs into a node may produce a multi-dimensional plane (e.g., hyperplane) to delineate a combination of inputs that are active or inactive.

Although the present invention describes components and functions implemented in the embodiments with reference to particular standards and protocols, the invention is not limited to such standards and protocols. Other similar standards and protocols not mentioned herein are in existence and are considered to be included in the present invention. Moreover, the standards and protocols mentioned herein, and other similar standards and protocols not mentioned herein are periodically superseded by faster or more effective equivalents having essentially the same functions. Such replacement standards and protocols having the same functions are considered equivalents included in the present invention.

The present invention, in various embodiments, configurations, and aspects, includes components, methods, uses, processes, systems and/or apparatus substantially as depicted and described herein, including various embodiments, sub combinations, and subsets thereof. Those of skill in the art will understand how to make and use the present invention after understanding the present disclosure. The present invention, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease, and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments, configurations, or aspects for the purpose of streamlining the disclosure. The features of the embodiments, configurations, or aspects of the invention may be combined in alternate embodiments, configurations, or aspects other than those discussed above. This method of disclosure is not to be interpreted as reflecting an intention that the claimed invention requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the invention.

Moreover, though the description of the invention has included description of one or more embodiments, configurations, or aspects and certain variations and modifications, other variations, combinations, and modifications are within the scope of the invention, e.g., as may be within the skill and knowledge of those in the art, after understanding the present disclosure. It is intended to obtain rights, which include alternative embodiments, configurations, or aspects to the extent permitted, including alternate, interchangeable and/or equivalent structures, functions, ranges, or steps to those claimed, whether or not such alternate, interchangeable and/or equivalent structures, functions, ranges, or steps are disclosed herein, and without intending to publicly dedicate any patentable subject matter.

In the foregoing description, for the purposes of illustration, methods were described in a particular order. It should be appreciated that in alternate embodiments, the methods may be performed in a different order than that described without departing from the scope of the embodiments. It should also be appreciated that the methods described above may be performed as algorithms executed by hardware components (e.g., circuitry) purpose-built to conduct one or more algorithms or portions thereof described herein. In another embodiment, the hardware component may comprise a general-purpose microprocessor (e.g., CPU, GPU) that is first converted to a special-purpose microprocessor. The special-purpose microprocessor then having had loaded therein encoded signals causing the, now special-purpose, microprocessor to maintain machine-readable instructions to enable the microprocessor to read and execute the machine-readable set of instructions derived from the algorithms and/or other instructions described herein. The machine-readable instructions utilized to execute the algorithm(s), or portions thereof may be limited but utilize a finite set of instructions known to the microprocessor. The machine-readable instructions may be encoded in the microprocessor as signals or values in signal-producing components by, in one or more embodiments, voltages in memory circuits, configuration of switching circuits, and/or by selective use of particular logic gate circuits. Additionally, or alternatively, the machine-readable instructions may be accessible to the microprocessor and encoded in a media or device as magnetic fields, voltage values, charge values, reflective/non-reflective portions, and/or physical indicia.

In another embodiment, the microprocessor further comprises one or more of a single microprocessor, a multi-core processor, a plurality of microprocessors, a distributed processing system (e.g., array(s), blade(s), server farm(s), "cloud," multi-purpose processor array(s), cluster(s), etc.) and/or may be co-located with a microprocessor performing other processing operations. Any one or more microprocessors may be integrated into a single processing appliance (e.g., computer, server, blade, etc.) or located entirely, or in part, in a discrete component and connected via a communications link (e.g., bus, network, backplane, etc. or a plurality thereof).

Examples of general-purpose microprocessors may comprise, a central processing unit (CPU) with data values encoded in an instruction register (or other circuitry maintaining instructions) or data values comprising memory locations, which in turn comprise values utilized as instructions. The memory locations may further comprise a memory location that is external to the CPU. Such CPU-external components may be embodied as one or more of a field-programmable gate array (FPGA), read-only memory (ROM), programmable read-only memory (PROM), erasable programmable read-only memory (EPROM), random access memory (RAM), bus-accessible storage, network-accessible storage, etc.

These machine-executable instructions may be stored on one or more machine-readable mediums, such as CD-ROMs or other type of optical disks, floppy diskettes, ROMs, RAMs, EPROMs, EEPROMs, magnetic or optical cards, flash memory, or other types of machine-readable mediums suitable for storing electronic instructions. Alternatively, the methods may be performed by a combination of hardware and software.

In another embodiment, a microprocessor may be a system or collection of processing hardware components, such as a microprocessor on a client device and a microprocessor on a server, a collection of devices with their respective microprocessor, or a shared or remote processing service (e.g., "cloud" based microprocessor). A system of microprocessors may comprise task-specific allocation of processing tasks and/or shared or distributed processing tasks. In yet another embodiment, a microprocessor may execute software to provide the services to emulate a different microprocessor or microprocessors. As a result, a first microprocessor, comprised of a first set of hardware components, may virtually provide the services of a second microprocessor whereby the hardware associated with the first microprocessor may operate using an instruction set associated with the second microprocessor.

While machine-executable instructions may be stored and executed locally to a particular machine (e.g., personal computer, mobile computing device, laptop, etc.), it should be appreciated that the storage of data and/or instructions and/or the execution of at least a portion of the instructions may be provided via connectivity to a remote data storage and/or processing device or collection of devices, commonly known as "the cloud," but may include a public, private, dedicated, shared and/or other service bureau, computing service, and/or "server farm."

Examples of the microprocessors as described herein may include, but are not limited to, at least one of Qualcomm® Snapdragon® 800 and 801, Qualcomm® Snapdragon® 610 and 615 with 4G LTE Integration and 64-bit computing, Apple® A7 microprocessor with 64-bit architecture, Apple® M7 motion microprocessors, Samsung® Exynos® series, the Intel® Core™ family of microprocessors, the Intel® Xeon® family of microprocessors, the Intel® Atom™ family of microprocessors, the Intel Itanium® family of microprocessors, Intel® Core® i5-4670K and i7-4770K 22 nm Haswell, Intel® Core® i5-3570K 22 nm Ivy Bridge, the AMD® FX™ family of microprocessors, AMD® FX-4300, FX-6300, and FX-8350 32 nm Vishera, AMD® Kaveri microprocessors, Texas Instruments® Jacinto C6000™ automotive infotainment microprocessors, Texas Instruments® OMAP™ automotive-grade mobile microprocessors, ARM® Cortex™-M microprocessors, ARM® Cortex-A and ARIV1926EJS™ microprocessors, other industry-equivalent microprocessors, and may perform computational functions using any known or future-developed standard, instruction set, libraries, and/or architecture.

Embodiments include a method of assessing a patient's response to a cancer treatment in a patient having a cancer, the method comprising: receiving a first image associated with the patient before administering the cancer treatment and automatically determining with a neural network a level of microbiomes in the first image; receiving a second image associated with the patient after administering the cancer treatment and automatically determining with a neural network a level of microbiomes in the second image; comparing the level of microbiomes in the first image the level of microbiomes in the second image, wherein a decrease in the level of microbiomes in the first image as compared to the level of microbiomes in the second image indicates the patient is responding to the cancer treatment, and wherein an increase in the level of microbiomes in the first image as compared to the level of microbiomes in the second image indicates the patient is not responding to the cancer treatment; and continuing treating the patient with the cancer treatment if there is a decrease in the level of microbiomes in the first image as compared to the level of microbiomes in the second image, or adjusting the cancer treatment if there is an increase in the level of microbiomes in the first image as compared to the level of microbiomes in the second image.

Embodiments further include a computer system for assessing a patient's response to a cancer treatment in a patient having a cancer, the system comprising: a processor; and a computer-readable storage medium storing computer-readable instructions which, when executed by a processor, cause the processor to: receive a first image associated with the patient before administering the cancer treatment and automatically determining with a neural network a level of microbiomes in the first image; receive a second image associated with the patient after administering the cancer treatment and automatically determining with a neural network a level of microbiomes in the second image; compare the level of microbiomes in the first image the level of microbiomes in the second image, wherein a decrease in the level of microbiomes in the first image as compared to the level of microbiomes in the second image indicates the patient is responding to the cancer treatment, and wherein an increase in the level of microbiomes in the first image as compared to the level of microbiomes in the second image indicates the patient is not responding to the cancer treatment; and continue treating the patient with the cancer treatment if there is a decrease in the level of microbiomes in the first image as compared to the level of microbiomes in the second image, or adjust the cancer treatment if there is an increase in the level of microbiomes in the first image as compared to the level of microbiomes in the second image.

Embodiments further include a computer system configured to execute a convolutional neural network to detect a level of microbiome in a whole slide image associated with the patient; based on an output of the convolutional neural network, categorize the whole slide image as one of microbiome-low and microbiome-high; and based on the categorization of the whole slide image, determine a characteristic of the cancer.

Aspects of the above method and computer system include wherein the whole slide image comprises hematoxylin and eosin (H&E) stained pathology slides.

Aspects of the above method and computer system include wherein the cancer is selected from the group consisting of head, neck, ovarian, and bladder cancer.

Aspects of the above method and computer system include wherein the convolutional neural network is trained based on FFPE diagnostic images from The Cancer Genome Atlas bladder cohort.

Aspects of the above computer system include wherein the output of the convolutional neural network is used to determine a patient survival statistic.

Aspects of the above computer system include wherein microbiome-low is associated with a microbiome level of less than about 390,000 and microbiome-high is associated with a microbiome level of greater than about 390,000.

Aspects of the above computer system include wherein the instructions further cause the processor to, based on the categorization of the whole slide image, determine the patient is responding to the cancer treatment and, in response to determining the patient is responding to the cancer treatment, continue treating the patient with the cancer treatment.

Aspects of the above computer system include wherein the instructions further cause the processor to determine a pathologic complete response (pCR) based on the output of the convolutional neural network.

Embodiments include a method of assessing a patient's response to a cancer treatment in a patient having a cancer, the method comprising: executing a convolutional neural network to detect a level of microbiome in a whole slide image associated with the patient; based on an output of the convolutional neural network, categorize the whole slide image as one of microbiome-low and microbiome-high; and based on the categorization of the whole slide image, determine a characteristic of the cancer.

Aspects of the above method and computer system include wherein the level of microbiomes in the image is determined based on an aggregation of results of processing a plurality of patches from the received first and second images. Aspects of the above method and computer system include wherein the first and second images comprise whole slide images (WSIs). Aspects of the above method and computer system include wherein an input to the one or more neural networks comprises a plurality of patches extracted from the WSIs. Aspects of the above method and computer system include wherein the first and second images comprise a 400×400 pixel image with 40× magnification. Aspects of the above method and computer system include wherein each patch of the plurality of patches is 100×100 microns in size. Aspects of the above method and computer system include wherein each patch of the plurality of patches comprises a one-hundred micrometer square patch. Aspects of the above method and computer system include wherein the neural network outputs a microbiome label for each of the plurality of patches. Aspects of the above method and computer system include wherein the level of microbiomes in the image comprises an aggregation of each microbiome label for each of the plurality of patches. Aspects of the above method and computer system include wherein the aggregation comprises a majority voting mechanism. Aspects of the above method and computer system include wherein the first and second images each comprise a frozen tissue image. Aspects of the above method and computer system include wherein the neural network is a convolutional neural network. Aspects of the above method and computer system include wherein images from The Cancer Genome Atlas (TCGA) train the convolutional neural network. Aspects of the above method and computer system include wherein the level of microbiomes is associated with microbial signatures in tissue and blood illustrated in the image. Aspects of the above method and computer system include automatically determining the level of cancer in the image comprises calculating a severity of cancer for the patient.

What is claimed is:

1. A computer system for assessing a patient's response to a cancer treatment wherein the patient has cancer, the system comprising:
- a processor; and
- a computer-readable storage medium storing computer-readable instructions which, when executed by a processor, cause the processor to:
  - process a whole slide image associated with the patient using a convolutional neural network trained to output one or more of a probability of an input whole slide image being microbiome-high and a probability of the input whole slide image being microbiome-low, wherein the whole slide image associated with the patient comprises hematoxylin and eosin (H&E)-stained pathology slides and the microbiome is a tumor-microenvironment TME-associated microbiome;

in response to an output of the convolutional neural network based on the whole slide image associated with the patient, categorize the whole slide image associated with the patient as one of microbiome-low and microbiome-high; and based on the categorization of the whole slide image associated with the patient, determine a characteristic of cancer associated with the patient.

2. The system of claim 1, wherein the cancer is bladder cancer, head and neck cancer, or ovarian cancer.

3. The system of claim 2, wherein the convolutional neural network is trained based on Formalin-Fixed Paraffin-Embedded (FFPE) diagnostic images sourced from a bladder cohort.

4. The system of claim 1, wherein the instructions further cause the processor to determine a survival statistic of the patient based on the output of the convolutional neural network.

5. The system of claim 1, wherein microbiome-low is associated with a microbiome level of less than a median microbiome level of a cohort and microbiome-high is associated with a microbiome level of greater than the median microbiome level of the cohort.

6. The system of claim 1, wherein the instructions further cause the processor to:

determine the patient is responding to the cancer treatment based on the categorization of the whole slide image associated with the patient; and continue treating the patient with the cancer treatment in response to determining the patient is responding to the cancer treatment.

7. The system of claim 1, wherein the instructions further cause the processor to determine a pathologic complete response (pCR) based on the output of the convolutional neural network.

8. A method of assessing a patient's response to a cancer treatment wherein the patient has cancer, the method comprising:

processing a whole slide image associated with the patient using a convolutional neural network trained to output one or more of a probability of an input whole slide image being microbiome-high and a probability of the input whole slide image being microbiome-low, wherein the whole slide image associated with the patient comprises hematoxylin and eosin (H&E)-stained pathology slides and the microbiome is a tumor-microenvironment TME-associated microbiome;

in response to an output of the convolutional neural network based on the whole slide image associated with the patient, categorizing the whole slide image associated with the patient as one of microbiome-low and microbiome-high;

based on the categorization of the whole slide image associated with the patient, determining a characteristic of cancer associated with the patient;

determining the patient is responding to the cancer treatment based on the categorization of the whole slide image associated with the patient; and continuing treating the patient with the cancer treatment in response to determining the patient is responding to the cancer treatment.

9. The method of claim 8, wherein the cancer is bladder cancer, head and neck cancer, or ovarian cancer.

10. The method of claim 9, wherein the convolutional neural network is trained based on Formalin-Fixed Paraffin-Embedded (FFPE) diagnostic images sourced from a bladder cohort.

11. The method of claim 8, further comprising determining a patient survival statistic based on the output of the convolutional neural network.

12. The method of claim 8, wherein microbiome-low is associated with a microbiome level of less than a median microbiome level of a cohort and microbiome-high is associated with a microbiome level of greater than the median microbiome level of the cohort.

13. The method of claim 8, further comprising determining a pathologic complete response (pCR) based on the output of the convolutional neural network.

14. At least one machine-readable non-transitory medium comprising a plurality of instructions, executed on a computing device, to facilitate the computing device to:

process a whole slide image associated with the patient using a convolutional neural network trained to output one or more of a probability of an input whole slide image being microbiome-high and a probability of the input whole slide image being microbiome-low, wherein the whole slide image associated with the patient comprises hematoxylin and eosin (H&E)-stained pathology slides and the microbiome is a tumor-microenvironment TME-associated microbiome;

in response to an output of the convolutional neural network based on the whole slide image associated with the patient, categorize the whole slide image associated with the patient as one of microbiome-low and microbiome-high; and based on the categorization of the whole slide image associated with the patient, determine a characteristic of cancer associated with the patient.

15. The machine-readable non-transitory medium of claim 14, wherein the cancer is bladder cancer, head and neck cancer, or ovarian cancer.

16. The machine-readable non-transitory medium of claim 15, wherein the convolutional neural network is trained based on Formalin-Fixed Paraffin-Embedded (FFPE) diagnostic images sourced from a bladder cohort.

17. The machine-readable non-transitory medium of claim 14, wherein the instructions further facilitate the computing device to determine a survival statistic of the patient based on an output of the convolutional neural network.

18. The system of claim 1, wherein the convolutional neural network categorizes the whole slide image based on a percentage of image patches classified by the convolutional neural network as being one of microbiome-high or microbiome-low.

19. The system of claim 18, wherein categorizing the whole slide image further comprises the convolutional neural network generating a patch-based result that comprises an indication for each image patch as being one of microbiome-high or microbiome-low.

20. The system of claim 1, wherein the instructions further comprise generating, by the convolutional neural network, the plurality of image patches associated with the whole slide image associated with the patient.

* * * * *